United States Patent [19]
Bryant et al.

[11] Patent Number: 5,772,085
[45] Date of Patent: Jun. 30, 1998

[54] FREE FLOW AEROSOL VALVES

[75] Inventors: Andrew M. Bryant, Loughborough, Great Britain; Nicholas C. Miller, White Bear Lake, Minn.; Peter D. Hodson, Trowell, Great Britain

[73] Assignee: Minnesota Mining and Manufacturing, St. Paul, Minn.

[21] Appl. No.: 612,593

[22] Filed: Mar. 8, 1996

Related U.S. Application Data

[63] Continuation-in-part of Ser. No. 401,965, Mar. 10, 1995, abandoned.

[51] Int. Cl.[6] .................................................. B65D 83/00
[52] U.S. Cl. ........................................ 222/402.2; 222/162
[58] Field of Search ................................. 222/402.2, 162

[56] References Cited

U.S. PATENT DOCUMENTS

| | | | |
|---|---|---|---|
| 2,772,814 | 12/1956 | Meyers | 222/82 |
| 3,126,132 | 3/1964 | Lyon et al. | 222/355 |
| 3,176,887 | 4/1965 | Potapenko et al. | 222/402.2 |
| 3,176,889 | 4/1965 | Potapenko et al. | 222/394 |
| 3,190,508 | 6/1965 | Petersen | 222/394 |
| 3,201,081 | 8/1965 | Lyon et al. | 251/172 |

FOREIGN PATENT DOCUMENTS

| | | |
|---|---|---|
| 0186280 | 7/1986 | European Pat. Off. . |
| 1 225 163 | 6/1960 | France . |
| 1261627 | 4/1961 | France . |
| 1461685 | 12/1966 | France . |
| 2258576 | 8/1975 | France . |
| 3040641 | 5/1982 | Germany . |

*Primary Examiner*—Gregory L. Huson
*Attorney, Agent, or Firm*—Gary L. Griswold; Walter N. Kirn, Jr.; Jeffrey J. Hohenshell

[57] ABSTRACT

A metered dose dispensing valve is described that is particularly suitable for dispensing metered volumes of a pressurised aerosol formulation. The valve comprises a chamber, and a valve stem extending into the chamber and movable relative to the chamber between non-dispensing and dispensing positions. The valve stem has a configuration and the chamber has an internal configuration such that a metered volume is defined therebetween and such that during movement between its non-dispensing and dispensing positions the valve stem sequentially: (i) allows free flow of aerosol formulation into the chamber, (ii) defines a closed metered volume for pressurised aerosol formulation between the external surface of the valve stem and internal surface of the chamber, and (iii) moves with the closed metered volume within the chamber without decreasing the volume of the closed metered volume until the metered volume communicates with an outlet passage thereby allowing dispensing of the metered volume of pressurised aerosol formulation.

18 Claims, 18 Drawing Sheets

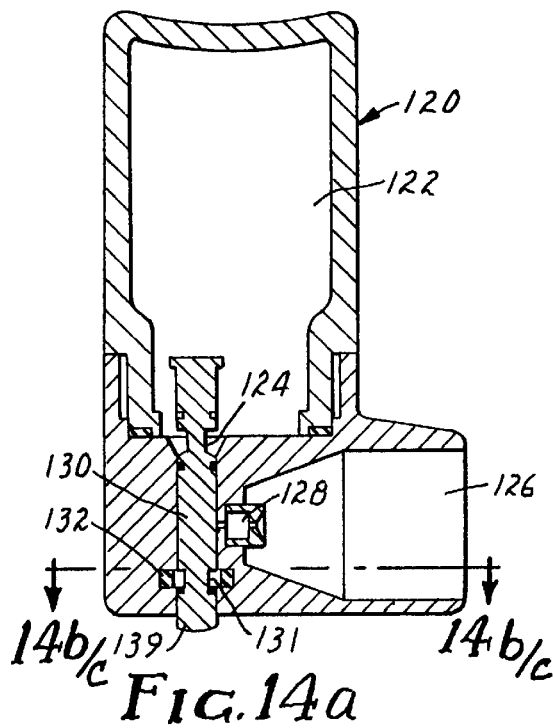
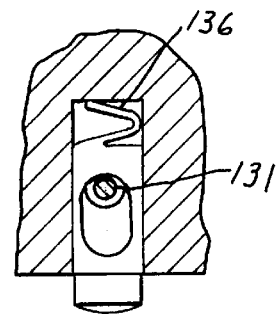
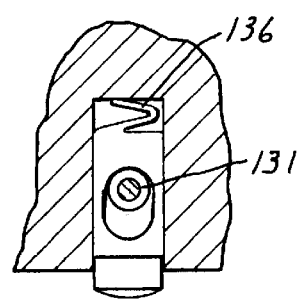
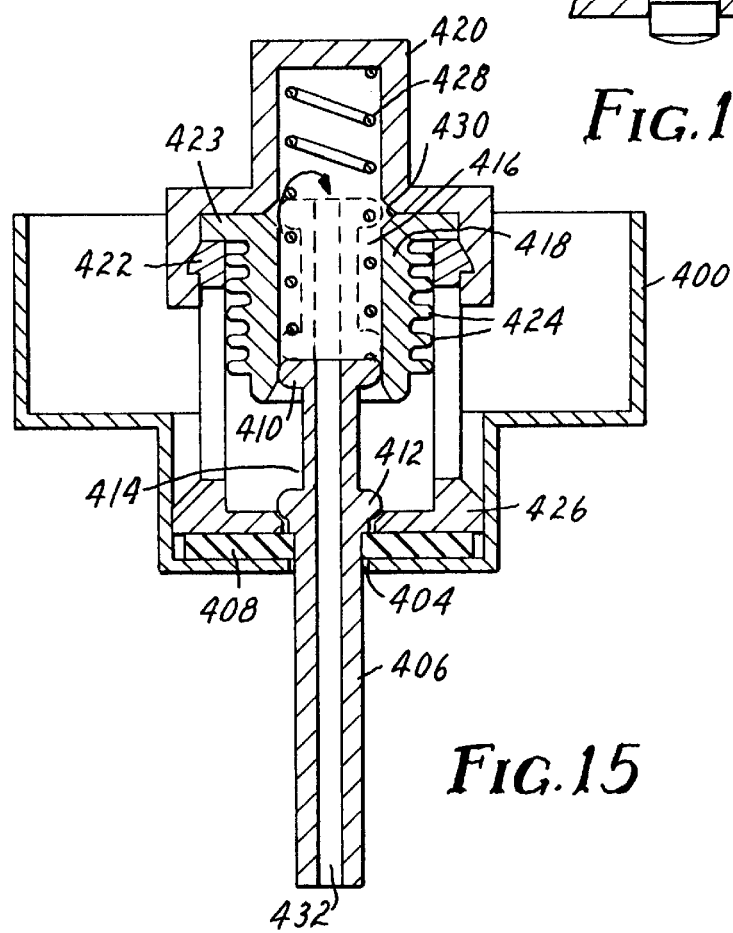

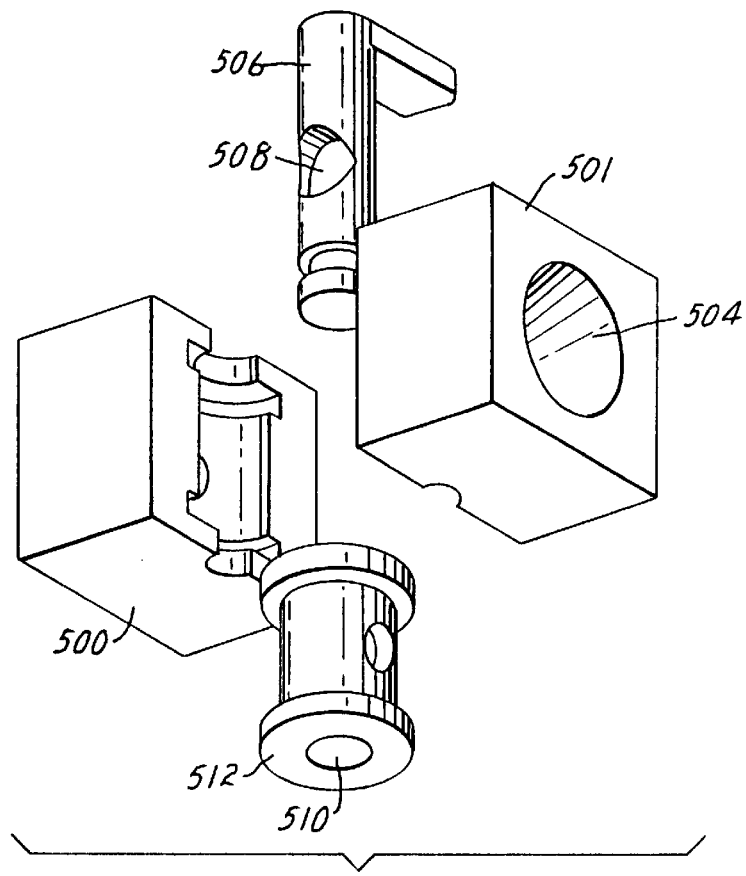
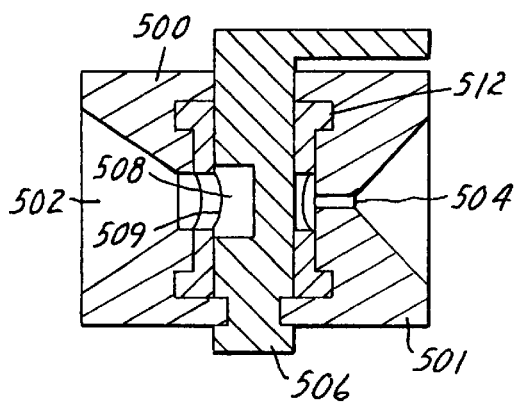 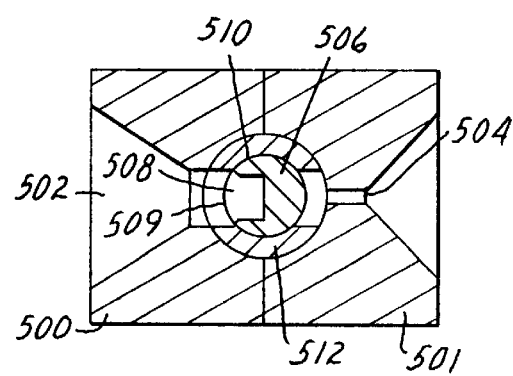
FIG.16c
FIG.16a          FIG.16b

5,772,085

FREE FLOW AEROSOL VALVES

RELATED APPLICATIONS

This application is a continuation-in-part of U.S. application Ser. No. 08/401,965, filed Mar. 10, 1995, and now abandoned which is incorporated by reference herein.

FIELD

This invention relates to a metered dose dispensing valve for dispensing metered volumes of a pressurised aerosol formulation from an aerosol container. In particular, the invention relates to an aerosol valve suitable for dispensing metered doses of medicament for administration to the respiratory system of a patient.

BACKGROUND

The use of aerosol devices to administer drug or other therapeutically active compounds by inhalation therapy is common, particularly for the treatment of respiratory disorders, such as, asthma. Aerosol containers are charged with a self-propelling liquid composition comprising an aerosol propellant having medicament dispersed or dissolved therein and the container is equipped with a valve capable of discharging a metered amount of the self-propelling composition.

Metered dose valves which have been used on commercially available aerosol inhalers comprise a fixed metering chamber having a movable valve stem extending therethrough. When the valve stem is in its closed position, there is a path for pressurised aerosol formulation in the aerosol container to pass into the metering chamber. As the valve stem is moved to its dispensing position, communication between the metering chamber and aerosol container is blocked thereby defining a fixed volume of pressurised aerosol formulation within the metering chamber. Further movement of the valve stem causes a discharge orifice in the valve stem to enter the metering chamber thereby allowing the contents of the chamber to be expelled through the valve stem under the influence of the aerosol propellant. Thus, in this type of metering valve, the metered volume of the aerosol formulation remains effectively stationary and the valve stem is moved into the metered volume of formulation until a discharge orifice in the valve stem communicates with the metering chamber.

One potential problem with metering valves is loss of prime. This phenomenon occurs commonly in known metering valves of the type in which the metering chamber is refilled with formulation immediately after actuation and resetting of the valve. The formulation in the metering chamber is generally only in communication with the bulk formulation in the vial via a narrow or tortuous passage or passages. The formulation stored in the metering chamber may drain out during storage between dispensing of doses, depending on the orientation of storage of the unit. A "vapour lock" may then form in the metering tank, preventing further formulation from entering the tank. This is termed "loss of prime" and results in a reduction in dose shot weight from the unit. This problem may be pronounced under particular conditions e.g. if the valve is stored at certain angles, if the temperature changes, if there are vibrations, etc. Such a situation may also occur if gas bubbles are generated when the aerosol container is shaken. Reduced doses may be obtained until the valve has been reprimed by actuating it several times. Such a purging procedure is clearly wasteful of the aerosol formulation.

Another problem common to many prior art metering valves occurs when suspension aerosol formulations are involved. Depending on the relative density of the various constituents of the aerosol formulation, certain constituents may either float or sink into or out of the metering tank during storage, depending upon the orientation of the valve. As a result, the doses subsequently delivered will not contain the intended composition of formulation.

U.S. Pat. No. 3,591,059 discloses a metering valve for dispensing a quantity of fluid from a container, comprising a valve stem having an outlet chamber with an outlet opening; a valve body adapted for mounting on the container in a stationary position with respect to the container and including means for closing the mouth of the container; with the valve stem mounted in the valve body for reciprocation between a closed position and a charge position; and spring means for urging the valve stem towards the closed position; the valve stem and body including first means defining a dose chamber, the valve body including second means defining a bypass zone with the body about the stem; and the outlet opening of the stem being disposed relative to the bypass zone such that the dose chamber is in communication with the interior of the container and the outlet chamber is blocked from the interior of the container, when the stem is in said charge position, and the dose chamber is blocked from the outlet chamber when the stem is in the closed position, and the dose chamber is in communication with the outlet chamber through the bypass zone and the outlet opening, and the dose chamber is blocked from the interior of the container, when the stem is intermediate the charge and closed positions. The valve body and stem are designed to provide an initially rapid stem movement after charging to seal off the metering chamber from the container, and a subsequent slower stem movement to provide adequate time for full discharge of the metered dose. In the embodiments disclosed during movement of the stem from the charge to intermediate position there is a reduction in the closed volume for the fluid within the metering valve i.e. the arrangement attempts to compress the closed volume of fluid (normally liquid formulation). Such an arrangement is undesirable since high forces are required during operation of the valve.

The present invention provides a significant advancement in the art of metered dose dispensing valves.

BRIEF SUMMARY OF THE INVENTION

According to the present invention there is provided a metered dose dispensing valve for dispensing metered volumes of a pressurised aerosol formulation, the valve comprising:

a chamber, and a valve stem extending into the chamber and movable relative to the chamber between non-dispensing and dispensing positions, the valve stem having a configuration and the chamber having an internal configuration such that a metered volume is defined therebetween and such that during movement between its non-dispensing and dispensing positions the valve stem sequentially:
(i) allows free flow of aerosol formulation into said chamber,
(ii) defines a closed metered volume for pressurised aerosol formulation between the external surface of the valve stem and internal surface of the chamber, and
(iii) moves with said closed metered volume within the chamber without decreasing the volume of said closed metered volume until said metered volume communicates with an outlet passage thereby allowing dispensing of said metered volume of pressurised aerosol formulation.

The valve of the invention is simple and effective and involves the principle of moving a closed metered volume of aerosol formulation to a discharge position rather than moving the valve stem containing a discharge orifice into a metered volume of aerosol formulation. The closed metered volume does not decrease in volume during movement of the valve stem thereby avoiding hydraulic compression which would otherwise increase the force needed to operate the valve and fire the dose. The valve may have numerous different constructions and may readily be integrated with a spray nozzle or may form part of an inhalation device.

The valves of the invention are constructed to allow free flow of aerosol formulation into the chamber prior to moving and dispensing the metered volume i.e., while in the inoperative or closed position, aerosol formulation can freely enter or leave the chamber depending on the orientation of the valve under the effect of gravity without the flow of aerosol formulation being significantly impeded. Thus, the valves of the invention do not comprise narrow or tortuous passages through which the aerosol formulation must pass to reach the chamber since such passages would significantly impede the flow. The presence of narrow or tortuous passages through which aerosol formulation must pass to enter the chamber could provide sites for drug deposition and build up or regions where gas bubbles could be trapped, and such problems are obviated by the valves of the invention. Furthermore the free flow of aerosol formulation into the chamber avoids the possibility that the dispensed dose size of the valve is dependent upon the speed of actuation.

In one embodiment the valve of the invention comprises a housing having a wall defining the chamber, said chamber having an inlet having dimensions sufficient to allow free flow of aerosol formulation therethrough and an outlet, said valve stem comprising first and second sealing surfaces longitudinally spaced, each sealing surface capable of forming a gas-tight seal with the wall of the chamber, the valve stem and the chamber being configured such that during movement of the valve stem between the non-dispensing and dispensing positions the valve stem sequentially passes:
(i) a priming position in which said inlet is open allowing free access of aerosol formulation to the chamber and said first sealing surface prevents access of aerosol formulation to said outlet,
(ii) a metering position in which said second sealing surfaces blocks said inlet and said first sealing surface prevents access of aerosol formulation to said outlet, thereby defining a closed metered volume between said first and second sealing surfaces and the wall of the chamber,
(iii) a shuttling stage during which the valve stem moves with said closed metered volume within the chamber without decreasing the volume of said closed metered volume, to
(iv) a dispensing position in which said first sealing surface is positioned to allow access of aerosol formulation to said outlet.

In one embodiment of the invention in order to allow free flow of aerosol formulation into the chamber, the chamber is completely open to the aerosol formulation in the reservoir until the valve is actuated, thus preventing loss of dose or loss of prime.

The valve may be constructed such that the valve stem moves inwardly from its closed to dispensing position in a similar manner to conventional metering valves. However, it is equally possible to construct a valve in which the valve stem moves outwardly from its closed to dispensing positions. The valve stem may be biased to its open or closed position mechanically e.g. by a spring, or under influence of pressure generated by the contents of the aerosol container. However, the valve stem need not be biased to either position thereby allowing the position of the valve stem to be easily controlled by an external mechanism.

In one embodiment of the invention the valve stem comprises two longitudinally spaced valve sealing elements capable of making gas-tight seals with the internal surface of the chamber to define a closed metered volume between the seals, the external surface of the valve stem and the internal surface of the chamber.

In a further embodiment of the invention the valve stem comprises at least one recess or aperture and the chamber includes an internal sealing surface making a gas-tight seal with the valve stem, the internal sealing surface extending longitudinally a greater distance than the recess on the valve stem whereby the closed metered volume is defined by the recess and the sealing surface of the chamber. The valve stem may comprise a plurality of recesses or holes to define the metering volume or the recess may be in the form of a circumferential groove or channel, or the recess may be in the form of an aperture extending through the valve stem.

In accordance with a further embodiment the valve stem comprises at least one recess and a first seal capable of making a gas-tight seal with the internal surface of the chamber, a second seal capable of making a gas-tight seal between the internal surface of the chamber and the valve stem being present on the valve stem or associated with the chamber such that the closed metered volume is defined between the recess, said first and second seals and the internal surface of the chamber.

The outlet passage from the chamber may extend radially through the chamber wall to an outlet nozzle or orifice. Alternatively, the outlet passage may direct the aerosol formulation to a different area of the valve from whence it may exit the valve via an additional discharge passage e.g. a passage in the valve stem.

In order to produce low sliding frictional forces during movement of the valve stem it is advantageous to employ an annular sealing element around the valve stem or wall of the chamber, which sealing element has a configuration which facilitates deformation in response to the forces generated during movement thereby reducing the frictional forces and maintaining a gas-tight seal. Such an annular sealing element is formed of resiliently deformable material and is preferably located around the valve stem e.g. positioned within a circumferential groove on the stem.

A variety of configurations of the annular sealing element are possible which facilitate deformation. For example, the annular sealing element may be in the form of an endless strip having a U-shaped or ring-shaped cross-section such that the hollow or internal space within the U-shape or ring-shape accommodates deformation when forces are exerted on the sealing element during movement of the valve stem. Alternatively, the sealing element may comprise an endless strip having a waist i.e. a thinner region intermediate the radially inner and outer peripheries which facilitates deformation of the strip. In a further embodiment, the annular sealing member comprises an endless strip having a substantially cruciform cross-section, preferably with the ends of the arms of the cross being rounded. Two arms of the cross may provide sealing surfaces, the arms readily being capable of deforming under the forces generated during movement of the valve stem.

In a further embodiment, the annular sealing member has a configuration which provides a small sealing surface e.g. the radially outer periphery has one or more circumferential projections which engage the wall of the passage or chamber to form a gas-tight seal.

When such annular sealing elements are located within a circumferential groove on the valve stem, the groove may be configured to provide free space to accommodate movement of the sealing elements when they are deformed, thereby reducing frictional forces. For example, the grooves may have a configuration selected from a flared opening, one or more recesses in the base of the groove, or in combination of these features.

BRIEF SUMMARY OF THE DRAWINGS

The invention will now be described with reference to the accompanying drawings in which:

FIG. 14a represents a longitudinal cross-section through an inhaler incorporating a valve in accordance with the invention, FIGS. 14b and 14c represent detailed sections along line A—A, FIG. 15 represents a longitudinal cross-section through a further valve in accordance with the invention, FIGS. 16a, b and c represent longitudinal and transverse cross-sections and an exploded view respectively of a rotary valve in accordance with the invention.

DETAILED DESCRIPTION

Figure 1A:
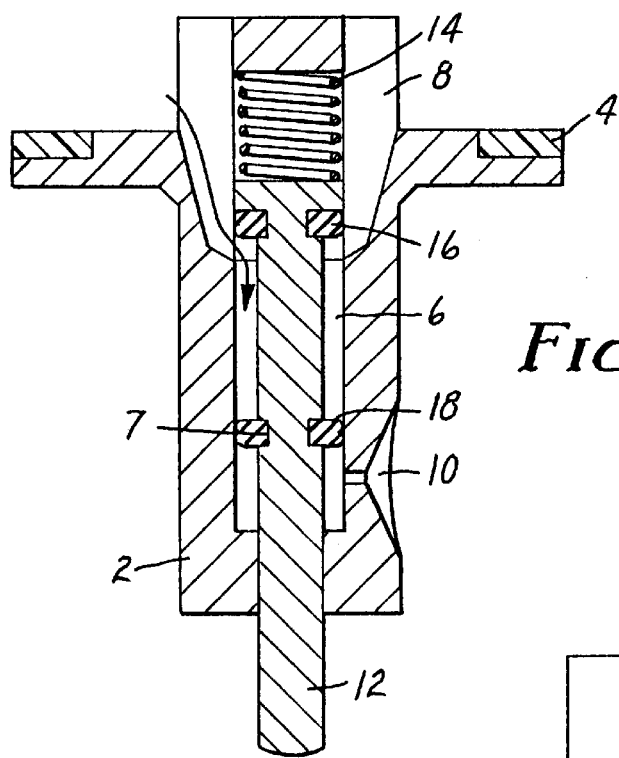
FIGS. 1a and 1b represent a longitudinal cross-section through a valve in accordance with the invention in its priming and dispensing positions respectively.
Figure 1B:
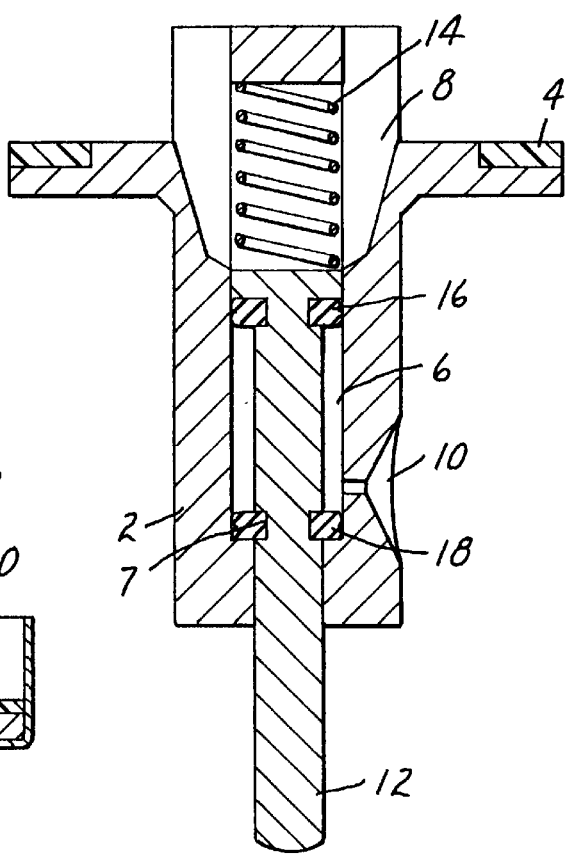

Referring to FIGS. 1a and 1b a valve of the invention comprises a body (2) having an annular seal or gasket (4) for engaging the neck of an aerosol container (not shown) to facilitate a gas-tight seal. The body (2) may be secured to the aerosol container by any suitable means e.g. a conventional outer casing or ferrule (not shown) which is crimped around the neck of the aerosol container.

The body (2) defines a chamber (6) having an inlet passage (8) and an outlet passage (10) for dispensing pressurised aerosol formulation. A valve stem (12) extends through the chamber (6) and is movable between a closed or priming position shown in FIG. 1a and a dispensing position as shown in FIG. 1b. The valve stem (12) is biased to its dispensing position by means of a spring (14). The valve stem (12) is fitted with an inner seal (16) and outer seal (18) which provide gas-tight seals between the valve stem and the inner wall of the chamber (6). The chamber (6), external dimensions of the valve stem (12) and position of the seals (16 and 18) are arranged to define a pre-determined volume within the chamber (6) between the seals (16 and 18).

In operation the valve stem (12) is moved inwardly against the bias of the spring (14) to the priming position shown in FIG. 1a. In the closed or priming position, aerosol formulation contained in the aerosol can or vial may freely enter or leave the chamber via the annular inlet between the seal (16) and the open end of the chamber as depicted by the arrow. With the aerosol unit held in this valve-down orientation, the design of the valve readily allows satisfactory doses to be obtained even when the aerosol vial is nearly empty, thereby preventing significant wastage of formulation. The inlet (8) is positioned at a level allowing substantially complete emptying of the aerosol container.

When the valve stem (12) is released it moves to its dispensing position shown in FIG. 1b under the influence of the spring (14). During this movement, the valve seal (16) enters the chamber (6) thereby trapping a metered volume of aerosol formulation between the seals (16 and 18) and the wall of the chamber. Further movement of the valve stem moves the metered volume of formulation along the chamber until the valve seal (18) passes the outlet passage (10) thereby allowing the outlet passage (10) to communicate directly with the metered volume of formulation as shown in FIG. 1b. The formulation is self-propelling and is sprayed through the outlet passage (10) under the influence of the vapourising aerosol propellant. The outlet passage (10) may incorporate one or more small orifices, as shown, to aid break-up of the spray without the need for a separate adapter orifice. An expansion chamber may be provided between two such orifices through which the spray passes sequentially, in order to further aid production of a fine respirable spray of drug containing particles, as shown in FIG. 14a described hereinafter.

The metered volume of formulation is not subjected to compression nor expansion during actuation of this valve, thus there is no hydraulic compression force which must be overcome to operate the valve, nor is there any tendency for the formulation in the metered volume to cavitate nor boil during its entry into and movement along the chamber.

In order to produce low sliding frictional forces between the valve seals (16 and 18) and the internal wall of the chamber (6) the configuration of the seals and/or the grooves (7) on the valve stem in which the seals are retained may be designed to provide space into which the seals can deform without large frictional forces being produced whilst ensuring maintenance of an effective gas-tight seal. Such an arrangement also provides compensation for manufacturing tolerances in the production of components.

FIGS. 2a to 2i represent cross-sections through annular sealing elements suitable for use as the valve seals (16, 18) in the valve illustrated in FIG. 1 and other valves of the invention. The seals may be fabricated of any suitable resiliently deformable material including thermoset rubbers such as butyl rubber, butadieneacrylonitrile rubber and neoprene, which are compounded with vulcanising agent prior to being fashioned into valve seals. Other useful sealing materials which are particularly suitable for use with Propellent 134a and/or Propellent 227 include thermoplastic elastomers comprising a copolymer of about 80 to 95 mol % ethylene with a comonomer selected from 1-butene, 1-hexene and 1-octene, which are disclosed in WO92/11190, ethylene-propylene-diene rubber disclosed in WO95/02651 and blend of (a) 100 parts by weight of a polyolefin random copolymer of about 80 to about 95 mole percent ethylene and a total of about 5 to about 20 mole percent of 1-butene, and (b) at least 10 parts by weight of a rubber comprising a styrene-ethylene/butylene-styrene block copolymer based on 100 parts by weight of polyolefin disclosed in WO95/03984.

Figure 2A:
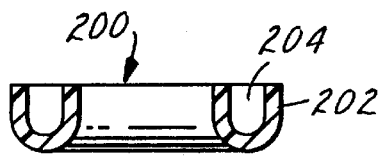
FIGS. 2a to 2i represent diametric cross-sections through sealing elements suitable for use in the invention.

The annular valve seal element (200) of FIG. 2a comprises a ring having a generally U-shaped cross-section with the arms of the U aligned with the central axis of the ring such that the outer face (202) of the U-shape provides the seal against the wall of the chamber. The internal space (204) of the U-shape can accommodate deformation of the outer face (202). It is advantageous to orientate the annular seal (202) such that the internal space (204) is exposed to the pressure of the aerosol formulation to facilitate sealing of the outer face.

Figure 2B:
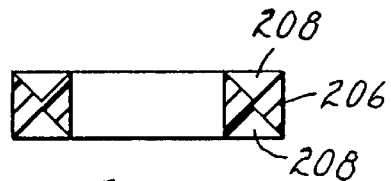

The annular sealing element of FIG. 2b has a "bow-tie" shaped cross-section i.e. as a square with triangles removed from the upper and lower sides. The outer sealing face (206) is intended to contact the wall of the chamber. The sealing element comprises grooves (208) which accommodate deformation of the outer circumferential portion of the sealing element without excessive build-up friction against the chamber wall.

Figure 2C:

FIG. 2c illustrates an annular sealing element having a circumferential sealing surface whose cross-section tapers to a point (210). The cross-section has the shape of a rectangle joined at the outer of its sides to the base of a triangle. Since the circumferential sealing surface formed by the point (210) is thin, it may readily be deformed against the wall of the chamber, thereby maintaining a gas-tight seal and minimising the surface area in contact with the wall of the chamber.

Figure 2D:
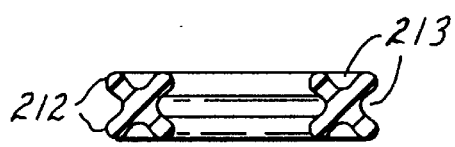

FIG. 2d illustrates an annular sealing element having a cruciform cross-section with rounded ends like that of a pair of dumbbells crossing each other orthogonally. When viewed in cross-section, the outer circumferential portion of the sealing element comprises two lobes (212) which contact the wall of the chamber. The sealing element additionally comprises recesses (213) which accommodate deformation of the lobes (212). The inner circumferential portion of the sealing element is similarly configured. The use of a plurality of lobes provides multiple sealing surfaces.

Figure 2E:
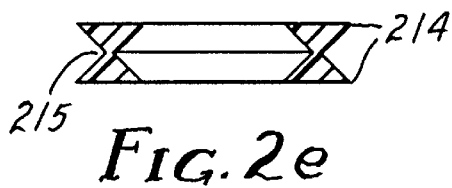

FIG. 2e illustrates an annular sealing element, which has a cross-section having the shape of a square with triangles removed from the radially inner and outer sides corresponding to the inner and outer surfaces. The outer circumferential configuration comprises two tapered portions (214) separated by a groove (215). The tapered portion which form sealing surfaces may be readily deformed in a similar manner to the design of FIG. 2c and the recess (215) may accommodate deformation of the portions (214). The inner circumferential configuration is similarly designed.

Figure 2F:
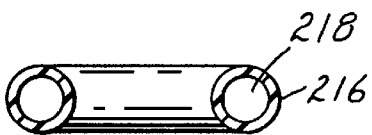

FIG. 2f illustrates an annular sealing element formed from a hollow circular tube. The outer circumferential sealing surface (216) which contacts the wall of the chamber may be deformed, the interior space (218) accommodating deformation of portion (216). The space (218) may optionally be filled with a compressible foam.

Figure 2H:
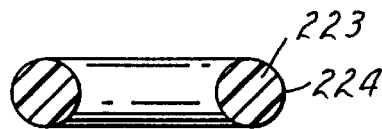
Figure 2G:
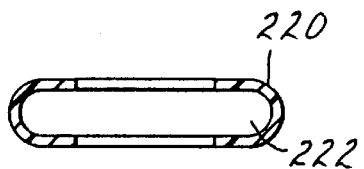

FIG. 2g shows an annular sealing element formed from a U-shaped tube disposed such that the base (220) of the U-shape forms the outer, circumferential sealing surface. The hollow space (222) within the U-shape accommodates deformation of the sealing surface (220).

FIG. 2h illustrates an annular sealing member formed from a ring having a core (223) of solid circular cross-section and a coating (224) of a low friction material e.g., polytetrafluoroethylene. The outer, circumferential sealing surface provides a low friction surface and a small surface area in contact with the wall of the chamber thereby reducing sliding frictional forces. Furthermore, the circular cross-section allows deformation of the sealing element under the forces generated.

Figure 2I:
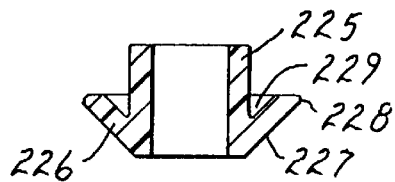

FIG. 2i illustrates an annular sealing element having a central cylindrical portion (225) which may be located around the valve stem and an annular skirt (226) having a conical surface (227). The outer circumferential sealing surface (228) contacts the wall of the chamber. The annular skirt is flexible thereby reducing frictional forces. The sealing element is advantageously positioned such that the internal space (229) is exposed to the pressure of the aerosol formulation to facilitate sealing. The sealing element is particularly advantageous since it may additionally function as a pressure filling valve as it will deflect inwardly under high pressure acting on the conical surface (227).

As an alternative, or in addition to the sealing element having a configuration which will accommodate deformation of the seal, the groove (7) of the stem (12) in which the seal is located may have a profile which provides space to accommodate deformation or swelling of the sealing element.

The following description of FIGS. 3a to 3f assumes the grooves will be occupied by annular sealing elements of rectangular cross-section.

Figure 3A:
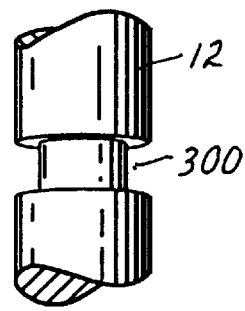
FIGS. 3a to 3f represent isometric views of parts of valve stems suitable for use in valves of the invention.

FIG. 3a illustrates a circumferential groove in the valve stem having sides at right angles to the outer surface of the stem. This arrangement does not provide scope to accommodate deformation of the valve seal under compression unless the seal does not completely occupy the volume of the groove (300).

Figure 3D:
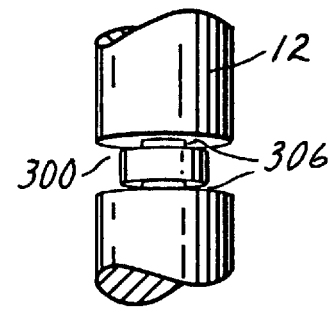
Figure 3B:
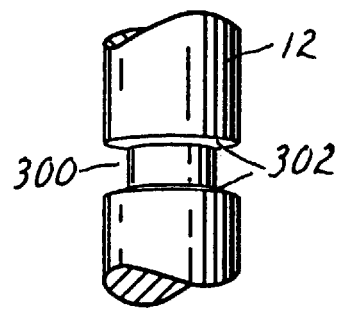

FIG. 3b discloses a similar arrangement to FIG. 3a with the exception that the side walls (302) of the groove (300)

are sloped such that the groove is flared in the radially outward direction. The groove (300) is wider than the sealing element in the vicinity of the sealing surface and has unoccupied space to accommodate deformation of the seal in that region.

Figure 3E:
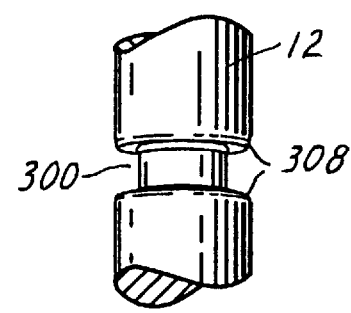
Figure 3C:
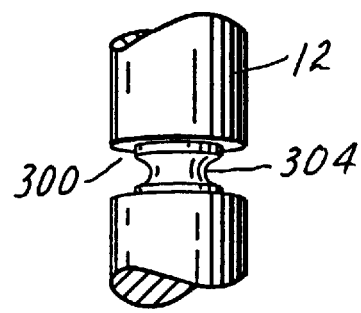

FIG. 3c illustrates a valve stem having a groove (300) for retaining the seal which is similar to that of FIG. 3a with the exception that the base of the groove is provided with a recess (304) of semi-circular cross-section. The recess (304) provides a space into which the sealing material can move when it is deformed.

FIG. 3d illustrates a groove (300) in the valve stem which is similar to that of FIG. 3a with the exception that two smaller circumferential grooves (306) of rectangular cross-section are provided at each end of the narrower part of the stem. These smaller grooves (306) provide free space to accommodate movement of the sealing element housed in groove (300) when the sealing element is deformed.

FIG. 3e illustrates a groove in the valve stem similar to that of FIG. 3a in which the radially outer portions of the walls are chamfered (308) thereby providing a space adjacent to the sealing surface of the sealing element to accommodate deformation of the sealing element. The radially inner portion is also chamfered.

Figure 3F:
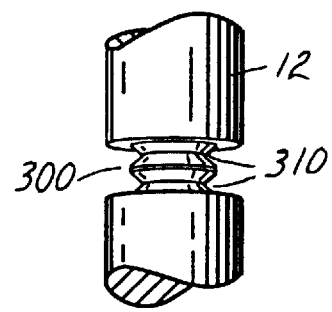

FIG. 3f illustrates part of a valve stem (12) having a circumferential groove (300). The groove is similar to that of FIG. 3d with the exception that the two smaller circumferential grooves (310) are of triangular cross-section.

In the interests of clarity the figures illustrating the aerosol valves in the accompanying drawings depict the valve seals and circumferential grooves for retaining the seals on the valve stem in a simplistic manner. It will be appreciated that embodiments of the valve seals illustrated in FIGS. 2a to 2i and embodiments of circumferential grooves illustrated in FIGS. 3a to 3f may be employed in appropriate positions on many of the illustrated valves.

Figure 4:
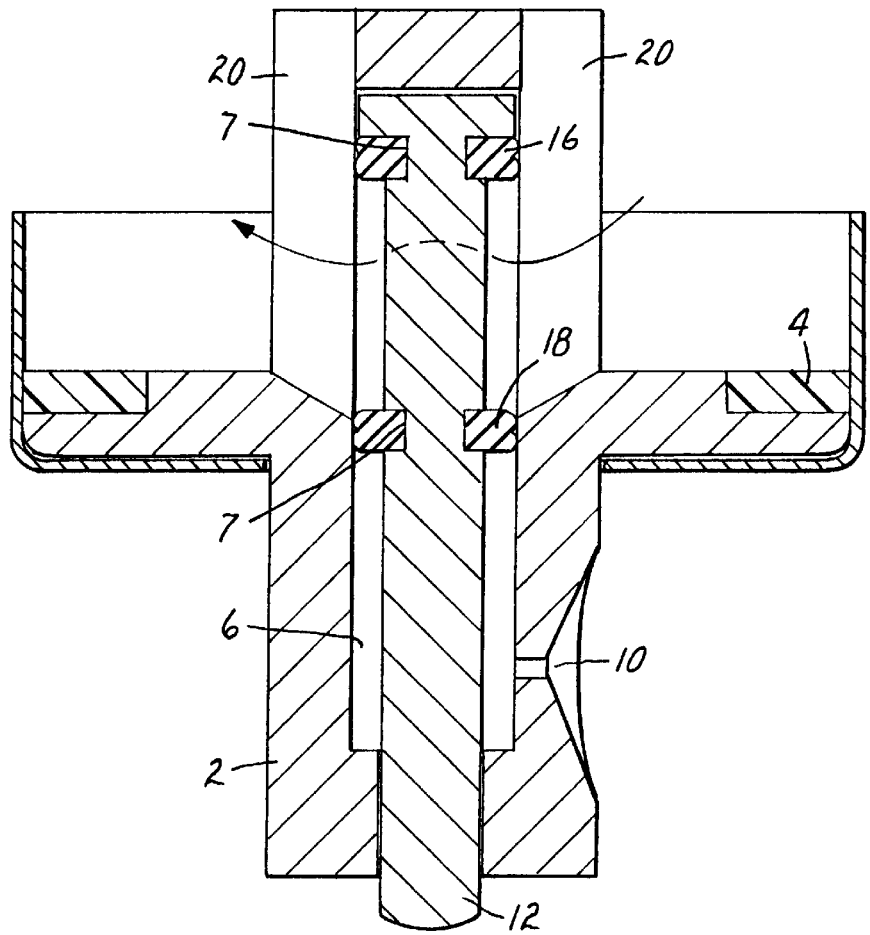
FIGS. 4 and 5 represent longitudinal cross-sections through different valves in accordance with the invention which are actuated by moving the valve stem outwardly.

The valve illustrated in FIG. 4 is similar to that shown in FIGS. 1a and 1b with the exception that in its priming or closed position the space between the seals (16 and 18) around the valve stem (12), extends further into the reservoir containing aerosol formulation. In addition, no biasing spring is used, but instead the valve stem is biased outwards to its dispensing position (not shown) by the action of the propellant vapour pressure. FIG. 4 shows the closed position of the valve. The alignment of the valve stem is ensured by ribs (20) which do not obstruct the free flow of aerosol formulation around the valve stem (12) between the seals (16 and 18). As the valve stem (12) moves downwardly to its dispensing position (not shown), the seal (18) moves down the chamber allowing free access of the aerosol formulation in to the chamber (6). Further movement of the valve stem causes seal (16) to enter the chamber (6) thereby trapping a metered volume of aerosol formulation between the seals (16 and 18) and the interior wall of the chamber (6). When the valve stem reaches its dispensing position the seal (18) passes outlet passage (10) thereby allowing direct communication between the metered volume and the outlet passage (10) thereby allowing the metered volume of formulation to be dispensed.

The valve of FIG. 4 provides a simple effective arrangement for dispensing accurate volumes of aerosol formulation. The valve has relatively few components compared with many of the metering valves currently in commercial use. Furthermore, the metered volume of formulation in the valve is not sealed off from the rest of the formulation in the aerosol vial until the valve stem is moved. Thus, potential problems of loss of prime, vapour or air locks, dose concentration and dose migration changes which may occur when a metering chamber is filled with formulation during storage of the device are avoided in the valve of the invention.

It will be appreciated that the seals (16, 18) may have any of the embodiments of FIGS. 2a to 2i and the grooves (7) in the valve stem may optionally have any of the configurations of FIGS. 3a to 3f.

Figure 5:
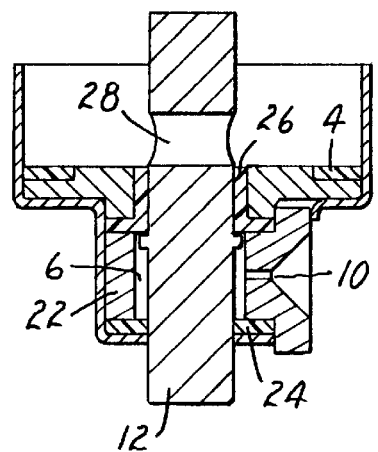

FIG. 5 illustrates a further valve in accordance with the invention in which the valve stem slides between stationary sealing surfaces. The chamber (6) is defined by a body (22) incorporating an outlet passage (10). At one end of the chamber is a stationary seal (24) providing a gas-tight seal with the valve stem (12). An elongate seal (26) is provided towards the upper end of the chamber which makes a gas-tight seal with the valve stem when the stem is in its closed or priming position as shown in FIG. 5. The valve stem (12) has an aperture (28) near its inner end. The aperture (28) extends longitudinally along the valve stem (12) less than the longitudinal length of the seal (26).

In the closed position of the valve illustrated in FIG. 5 entry of aerosol formulation into the aperture (28) is allowed, but entry of formulation into the chamber (6) is prevented. During movement of the valve stem downwardly towards its dispensing position, part of the aperture (28) enters the elongate seal (26) allowing aerosol formulation to move down into the space within the aperture (28) and inside the seal (26). Further movement of the valve stem (12) causes the entire aperture (28) to be accommodated within the seal (26) thereby trapping a metered volume of aerosol formulation between the seal (26) and the walls of the aperture (28) in the valve stem. Further movement of the valve stem to its dispensing position causes the lower portion of the aperture (28) to pass out of the seal (26) thereby allowing communication between the outlet passage (10) and the aerosol formulation in the aperture (28) which is dispensed through the passage (10) under the influence of the aerosol propellant.

The aperture (28) in the valve stem (12) of the valve illustrated in FIG. 5 may have a variety of configurations. FIGS. 6a to 6d illustrate valve stems having different configurations of recesses and apertures.

Figure 6A:
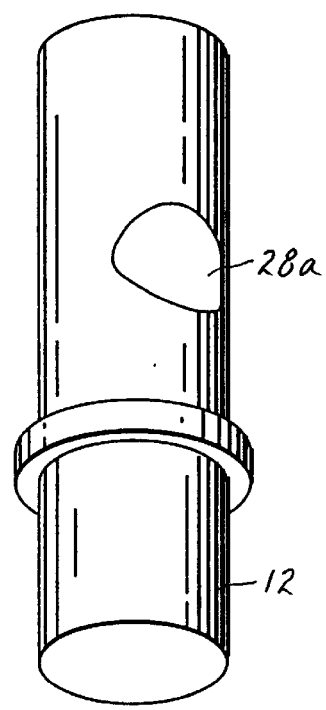
FIGS. 6a to 6d represent isometric views of valve stems suitable for use in the valve shown in FIG. 5, FIGS. 7a and 7b represent longitudinal cross-sections through a valve in accordance with the invention which is fired by moving the valve stem outwardly, FIG. 7a showing the priming position and FIG. 7b the dispensing position of the valve.

The valve stem of FIG. 6a has a simple circular aperture (28a) extending diametrically through the valve stem. The dimensions of the aperture are selected to define the desired metered volume to be dispensed.

Figure 6B:
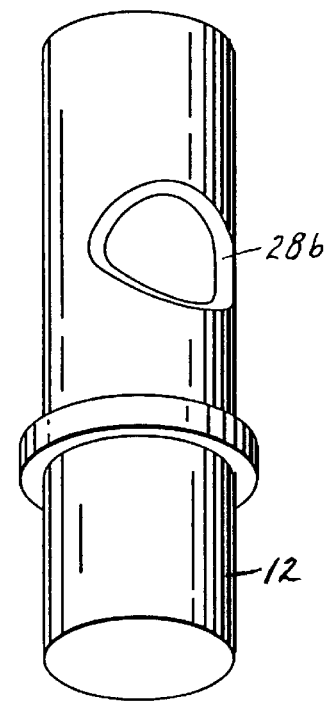

FIG. 6b illustrates a modification of the configuration of FIG. 6a in which the inlet to the aperture (28b) is filleted or chamfered, which facilitates movement of the sealing element over the aperture during movement of the valve stem.

Figure 6C:
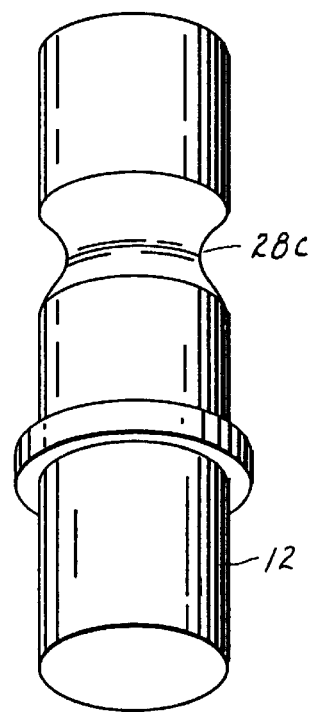

FIG. 6c illustrates an aperture (28c) in the form of a circumferential groove the dimensions of which are selected to define, with the sealing element (26), the desired metered volume to be dispensed.

Figure 6D:
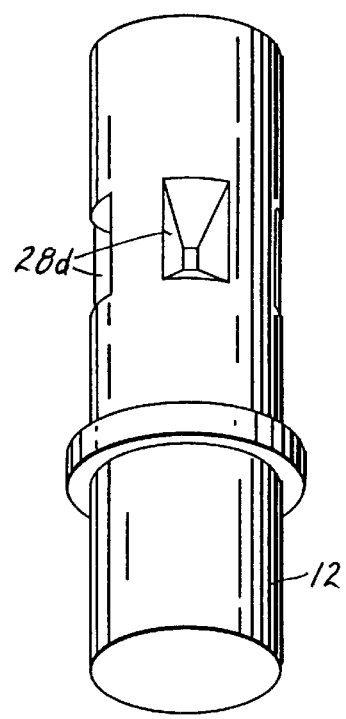

FIG. 6d illustrates an alternative valve stem comprising a plurality of indents or apertures (28d) which are spaced around the stem. The apertures (28d) are dimensioned to define the desired metered volume and each may optionally extend diametrically across the stem or communicate with one or more apertures.

It will be appreciated that all of the embodiments of the valve stems shown in FIG. 6a to 6d function in the identical manner described with reference to FIG. 5.

Figure 7A:
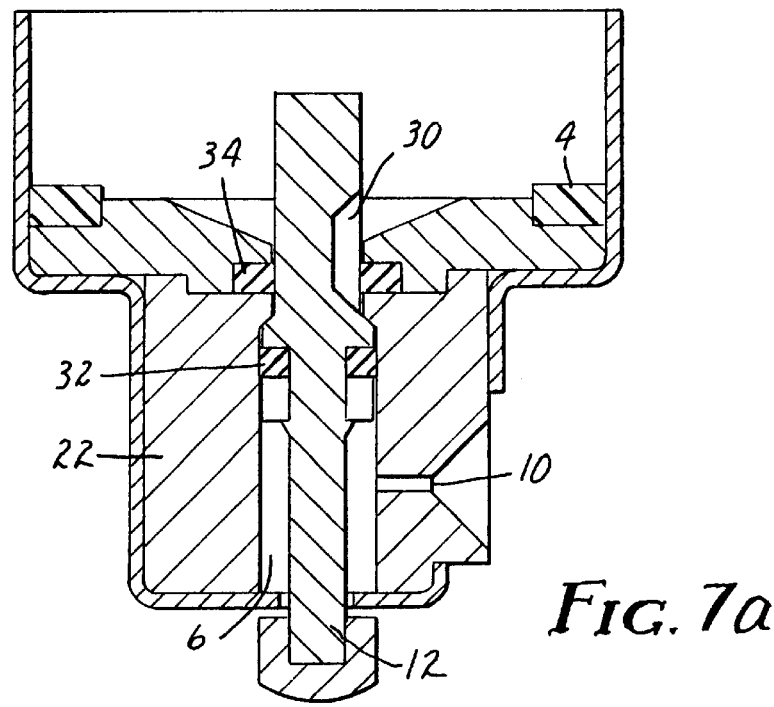
Figure 7B:
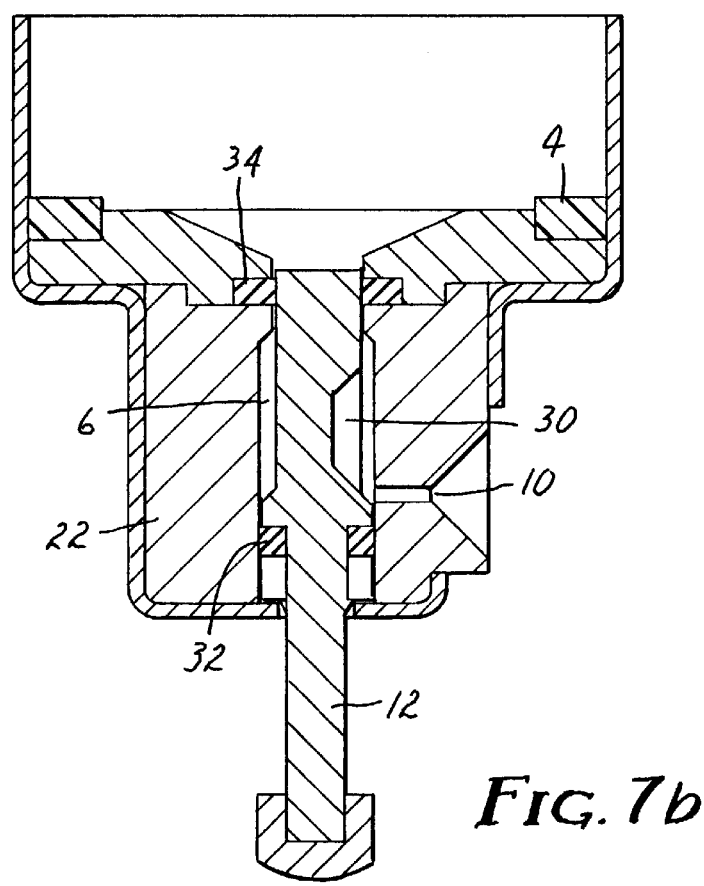

The valve of FIGS. 7a and 7b comprises a valve stem (12) having a lower seal (32) which is movable with the valve stem. The chamber (6) has a static seal (34) at its inner end. The valve stem (12) has a recess (30). In operation, the valve stem (12) moves downwards from its closed position as illustrated in FIG. 7a in which aerosol formulation has free access to the recess (30) towards its dispensing position shown in FIG. 7b during which recess (30) passes through the seal (34) thereby trapping a metered volume of aerosol formulation within the recess (30) between the seals (32 and 34). Further movement of the valve stem causes seal (32) to pass by the outlet passage (10) thereby allowing direct communication between the outlet passage (10) and the aerosol formulation contained within the recess (30) and chamber (6) causing dispensing of the formulation under the influence of the aerosol propellant. In this embodiment of the valve the metered quantity of aerosol formulation is allowed to expand in the chamber (6) prior to dispensing through the outlet passage.

It will readily be appreciated that FIGS. 4 to 7 do not illustrate the presence of a biasing means in the interests of clarity. The valve designs may readily have a spring bias as illustrated in FIGS. 1a and 1b, or the cross-section of the inner end of the valve stem may be arranged such that the pressure within the aerosol container biases the valve stem towards its dispensing position, as illustrated in FIG. 4, thereby not requiring a spring. Alternatively, the valve stem may be associated with external means to provide the valve stem with bias in either direction or a neutral bias. Such an external means may comprise an actuation mechanism for moving the valve stem to fire the valve. It will also be appreciated that the valve designs with springs shown in the following FIGS. may be modified to remove the spring from each design and use the aerosol propellant pressure instead to bias the stem. In addition, it will be understood that the valve designs shown are appropriate for use in the conventional "stem-down" orientation but could readily be adapted to work at other orientations if desired.

Figure 8A:
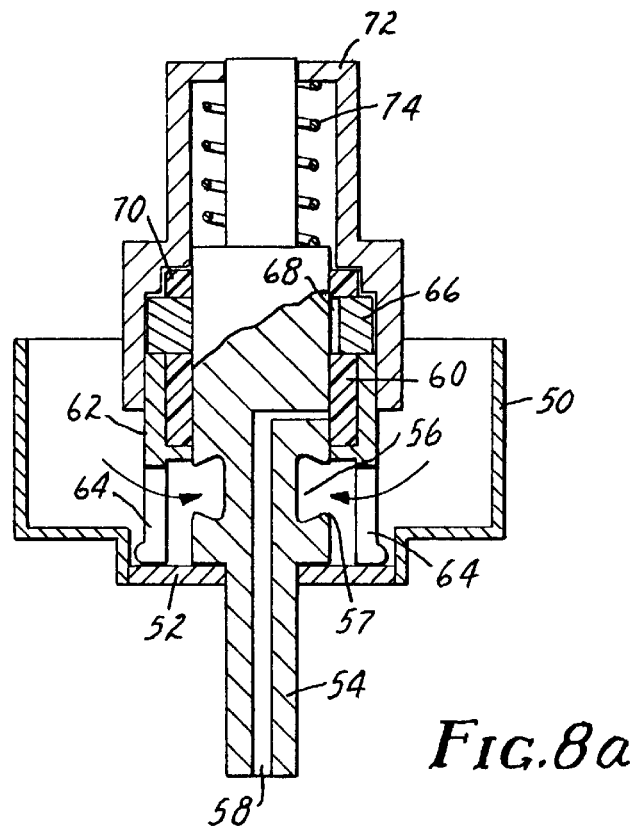
FIGS. 8a and 8b represent longitudinal cross-sections through a valve in accordance with the invention which is fired by moving the valve stem inwardly, FIG. 8a showing the priming position and FIG. 8b showing the dispensing position.
Figure 8B:
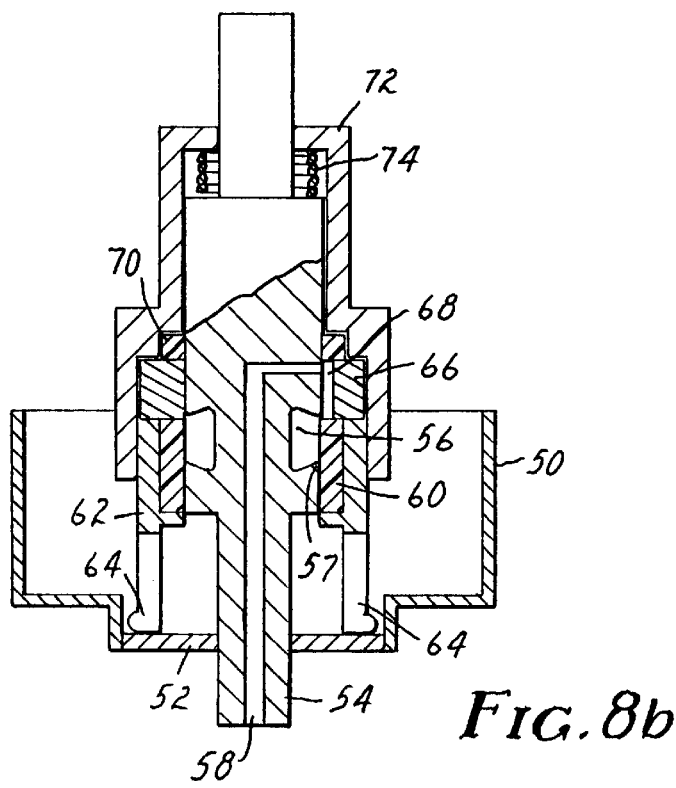

FIGS. 8a and 8b illustrate the principle of an aerosol valve in accordance with the invention which is fired by moving the valve stem inwardly in a similar manner to the conventional, commercially available metered dose valves used with pressurised aerosol inhalers.

FIGS. 8a shows the main components of the valve which comprises a mounting cup or ferrule (50), and a lower seal (52) through which extends a valve stem (54). The valve stem (54) is provided with a circumferential groove (56) defining an annular metering chamber and a dispensing passage (58). A chamber is defined by an elongate seal (60) which extends in the longitudinal direction by a length greater than the opening of the circumferential groove (56). The seal (60) is supported by a lower support member (62) having a plurality of legs (64) which allows the circumferential groove (56) to fill and empty readily with the aerosol formulation as the reservoir orientation changes when the valve is in its closed position as illustrated in FIG. 8a. An annular member (66) is positioned above the seal (60) to define a dispensing channel (68) between the annular member and the valve stem (54). An upper seal (70) makes a gas-tight seal with the exterior surface of the valve stem (54). An upper support (72) holds the annular member (66) and seal (70) in place and also captures spring (74) which biases valve stem (54) towards its closed position.

In operation, the valve stem (54) moves from the closed position shown in FIG. 8a to the dispensing position depicted diagrammatically in FIG. 8b. In FIG. 8b certain components have been omitted in the interests of clarity. As the valve stem (54) moves from its closed position, the circumferential groove (56) enters the seal (60) thereby trapping a metered volume of aerosol formulation between the groove (56) and the seal (60). Further movement of the valve stem causes both the passage (58) and the circumferential groove (56) to communicate with the dispensing channel (68) as shown in FIG. 8b. Thus, the dispensing channel is in communication with the aerosol formulation contained in the recess (56) and the aerosol formulation therein will be dispensed through the passage (58) as shown by the arrows in FIG. 8b. Again, loss of prime is not possible in this valve because there is free access of aerosol formulation to the metering chamber when the valve is in its nondispensing configuration. In addition, significant changes with time of concentration of aerosol formulation in the circumferential groove (56) are prevented by the rims (57) at the top and bottom edges of the circumferential groove. These rims tend to prevent any component of the formulation from floating or sinking out of or into the circumferential groove during storage.

Figure 9:
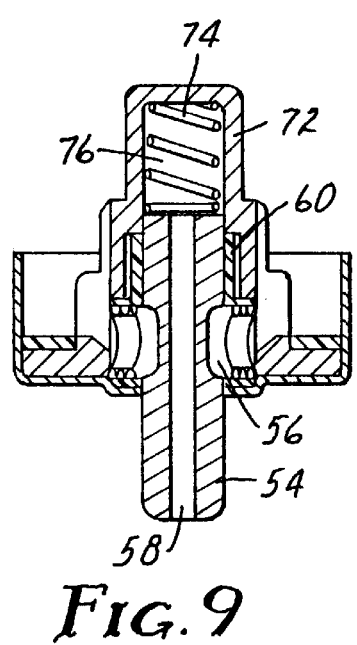
FIGS. 9 to 12 represent longitudinal cross-sections through valves in accordance with the invention which are actuated by moving the valve stem inwardly.

The valve illustrated in FIG. 9 operates in a similar manner to that shown in FIGS. 8a and 8b. The valve stem (54) has a circumferential recess (56), provided it is operated in the stem down orientation defining a metering chamber with the elongate seal (60). The outlet passage (58) extends through the valve stem (54) and the upper support (72) defines a transfer space (76). In operation, the valve stem (54) moves from its closed position as shown in FIG. 9 thereby trapping a metered volume of aerosol formulation within the recess (56) and the seal (60). Further movement of the valve stem causes the upper edge of the recess (56) to enter the transfer space (76) defined by the upper support member (72) thereby allowing communication between the outlet passage (58) and the recess (56). Aerosol formulation within the recess (56) will be dispensed through the outlet passage (58) via the transfer space (76) under the influence of the aerosol propellant.

Figure 10A:
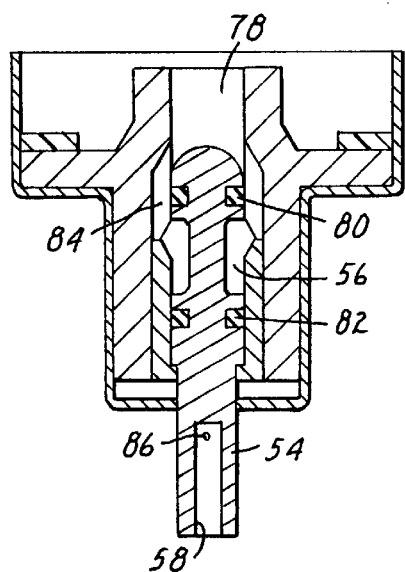
Figure 10B:
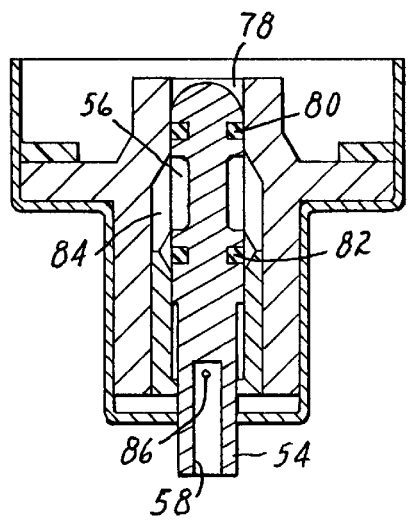

The valve illustrated in FIGS. 10a and 10b comprises a valve stem (54) having an outlet passage (58), a circumferential recess (56) and on either side of the recess (56) an upper seal (80) and a lower seal (82) which make a gas-tight seal with the internal wall of the chamber (78). The chamber is provided with passage (84) which may be an annular recess in the wall of the chamber or may be in the form of one or more longitudinal grooves. The valve is shown in FIG. 10a in its closed position which allows free access of aerosol formulation to the recess (56) via the passage (84).

As the valve stem (54) is moved inwardly towards its dispensing position the upper seal (80) passes the end of the passage (84) making a gas-tight seal within the chamber (78) thereby defining a metered volume of aerosol formulation within the recess (56) and between the upper and lower seals (80 and 82). Further movement of the valve stem causes the lower seal (82) to pass the lower extent of the passage (84) thereby allowing communication between the outlet passage (58) and the metered volume of aerosol formulation within the recess (56) via the outlet aperture (86) and passage (84) as shown in FIG. 10b. Thus aerosol formulation within the recess (56) will be dispensed from the outlet passage (58) under the influence of the aerosol propellant.

Figure 11:
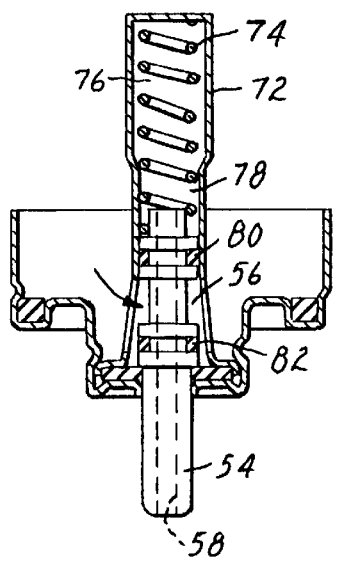

The valve illustrated in FIG. 11 comprises a valve stem (54) having a circumferential recess (56), an outlet passage (58) extending throughout its length and upper and lower seals (80 and 82) which make a gas-tight seal with the walls of the chamber (78). The wider part of the support component (72) defines a transfer space (76) and captures a spring (74) which biases the valve stem (54) to its closed position as shown in FIG. 11. In the closed position of the valve the aerosol formulation has free access to the circumferential recess (56). As the valve stem is moved towards its dispensing position, the lower seal (82) makes a gas-tight seal with the wall of the chamber (78) thereby trapping a metered volume of aerosol formulation in the recess (56) within the chamber (78) between the seals (80 and 82). Further movement of the valve stem towards the dispensing position causes the upper seal (80) to enter the transfer space (76) thereby allowing communication of the aerosol formulation within the recess (56) with the outlet passage (58) via the transfer space (76). The aerosol formulation will be discharged through the outlet passage (58) under the influence of the aerosol propellant.

Figure 12:
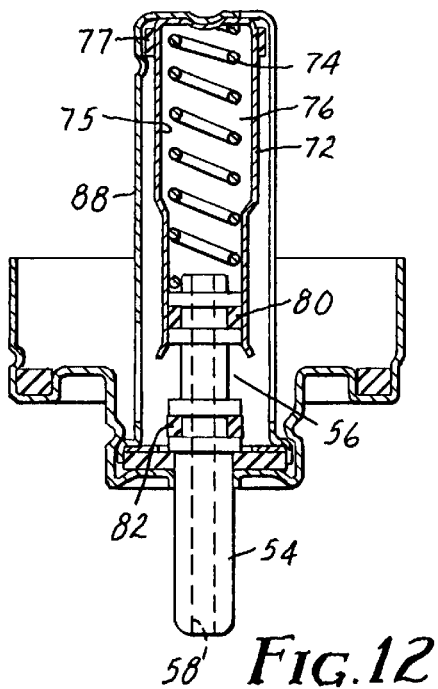

The aerosol valve shown in FIG. 12 operates in an identical manner to that shown in FIG. 11. The valve of FIG. 12 comprises an outer support member (88) which secures support member (72) thereby allowing a shorter support member (72) to be employed compared with the valve illustrated in FIG. 11. This arrangement allows free access of the aerosol formulation to the circumferential recess (56) since the outer support member has large openings in its walls, particularly around the circumferential recess (56). The shorter outer support member (72) is more readily formed by the deep-drawing process than is the longer support member (72) of the valve shown in FIG. 11.

The valve of FIG. 12 may also comprise a pressure filling valve in the form of aperture (75) covered by an elastomeric sleeve (77). The valve may be crimped to an aerosol container which may be filled through the valve stem (54) by introducing aerosol formulation under pressure through passage (58) into the transfer space (76) the pressure being sufficient to displace the elastomeric sleeve (77) from the aperture (75) allowing the aerosol formulation to enter the container.

Figure 13:
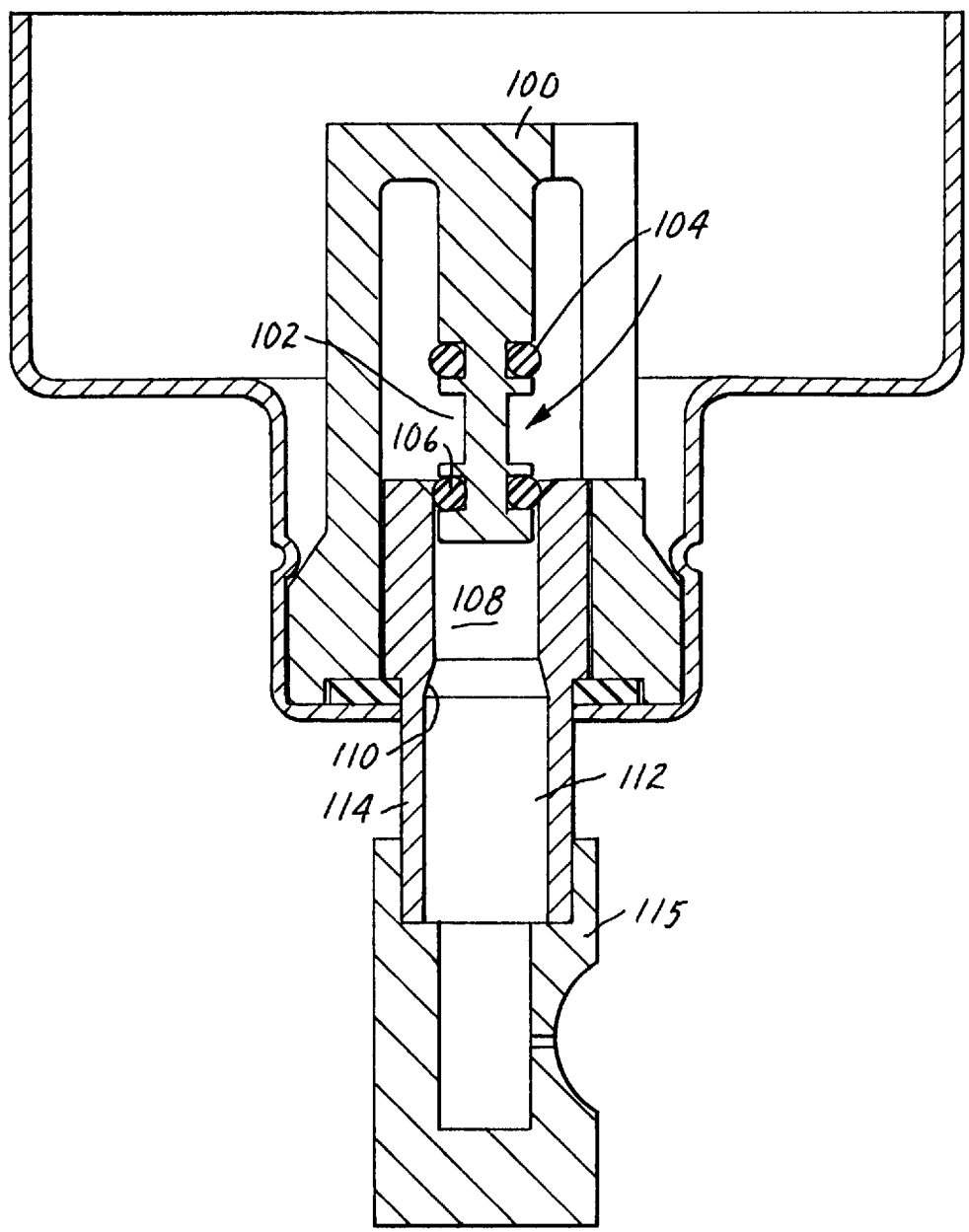
FIG. 13 represents a longitudinal cross-section through a further valve in accordance with the invention.

The valve illustrated in FIG. 13 employs a stationary valve stem and a movable chamber. The valve stem (100) comprises a circumferential recess (102) having on either side an upper seal (104) and lower seal (106) respectively. The seals (104 and 106) form a gas-tight seal within the chamber (108). At the outer end of the chamber is a passage (110) in the form of an annular recess or one or more longitudinally extending recesses. Outlet passage (112) is in an outer tube (114) communicating with the chamber (108). The outer tube (114) has mounted on its outer end a nozzle block (115).

The valve is shown in FIG. 13 in the closed position in which aerosol formulation has free access to the recess (102). In operation, the chamber (108) is moved inwardly relative to the valve stem (100) causing upper seal (104) to enter the chamber thereby trapping a metered volume of aerosol formulation in the recess (102) within the chamber (108) between the seals (104 and 106). Further movement of the chamber causes the lower seal (106) to enter the vicinity of the passage (110) thereby allowing communication between the outlet passage (112) and the recess (102) via the passage (110). Thus, aerosol formulation within the recess (102) will pass through the passage (110) and outlet passage (112) under the influence of the aerosol propellant.

FIG. 14a represents an aerosol inhaler incorporating a valve in accordance with the invention. The inhaler (120) comprises an aerosol container (122) equipped with a dispensing valve generally shown at (124). The inhaler has a mouthpiece (126) and an expansion chamber (128) directed into the mouthpiece. The aerosol valve has an elongate valve stem (130) and a latch mechanism generally shown at (132).

The valve (124) is similar to that shown in FIG. 4, the valve stem having sufficient cross-sectional area such that it is biased to its dispensing position under the influence of the pressurised aerosol formulation within the aerosol container or vial (122).

The valve stem is retained in its closed position by a latch mechanism which comprises a slider (133) which engages a narrow region (131) in the extended portion of the valve stem. The slider is retained in its engaged position by a biasing spring (136) which may be integrally formed with the slider (see FIGS. 14b and 14c). In order to actuate the device the patient breathes through the mouthpiece (126) and presses button (138) in the side of the inhaler (FIG. 14b) causing the slider (133) to move further into its recess (137). Movement of the slider (133) disengages the slider from the narrow region (131) of the valve stem (130) (as shown in FIG. 14c) thereby allowing movement of the valve stem under the influence of the pressurised aerosol formulation from its closed to its dispensing position thereby dispensing a dose of aerosol formulation through the expansion chamber (128) into the mouthpiece (126). Thereafter, the valve stem is manually returned to its closed position by pushing button (139) on the end of the stem (130) causing engagement of the slider (133) with the narrow region (131) of the stem under the influence of the biasing spring (136).

It will be appreciated that aerosol valves of the invention may be used in conjunction with a wide range of devices e.g. devices triggering dispensing or causing actuation of the valve including pneumatic, hydraulic, mechanical, electrical and electro-mechanical operating devices which move the valve stem relative to the chamber or prevent movement of the valve stem until the required time. Such devices may be breath actuated to co-ordinate the dispensing of the medicament with inhalation by the patient.

FIG. 15 represents a longitudinal section through a further valve in accordance with the invention. The valve comprises a mounting cup (400) for securing the valve to an aerosol vial (not shown).

The mounting cup (400) has an aperture (404) through which extends the valve stem (406) in sealing engagement with seal (408). The valve stem (406) comprises upper and lower annular projections (410 and 412) defining a cylindrical recess (414) therebetween. Chamber (416) is defined by cylindrical walls (418) of an elastomeric sealing material. The inside diameter of the sealing material (418) is dimensioned to form a gas-tight seal with the annular projections (410 and 412).

The sealing material (418) forming the walls of the chamber (416) is held in position by upper and lower support members (420 and 422) which together define a recess accommodating a circumferential flange (423) on the sealing material (418). The sealing material (418) possesses a plurality of fins (424) which bear against the lower support (422) to allow some flexing of the sealing material (418) whilst providing sufficient lateral support for the chamber (416). The base (426) of the lower support (422) rests on the seal (408) and is dimensioned to prevent undesirable flexing of the seal (408). The valve stem (406) is biased to its non-dispensing position by spring (428) which acts between the upper support (420) and the inner end of the valve stem (406).

FIG. 15 shows the valve stem in its non-dispensing position in solid line and in its dispensing position in dashed outline. In the nondispensing position, the contents of the aerosol container have free access to the recess (414) between the annular projections (410 and 412). As the valve stem (406) is moved towards its dispensing position, the annular projection (412) will enter the chamber (416) making a gas-tight seal with the sealing material (418) thereby trapping a closed volume of aerosol formulation within the recess (414) defined between the upper and lower annular projections (410 and 412) and the sealing material (418) forming the chamber (416). Further movement of the valve stem (406) causes movement of the closed volume upwardly through the chamber (416) until the upper annular projection (410) passes out of the chamber (416) into a circumferential passage (430). The circumferential passage (430) allows the aerosol formulation within the chamber to exit through the passage (430) and pass out of the valve via the discharge passage (432) in the valve stem (406) as indicated by the arrow.

FIGS. 16a to 16c disclose a further valve in accordance with the invention in which the valve stem is capable of rotary motion. The valve comprises a nozzle block (500, 501) having a wide passage (502) in communication with an aerosol vial (not shown). The nozzle block (500, 501) has an outlet passage (504) for discharge of the pressurised aerosol formulation.

An elastomeric sealing element (512) is positioned within the nozzle block (500, 501) and is fixed relative to the nozzle block (500, 501). A chamber (510) is defined by the inside walls of the elastomeric sealing element (512).

A valve stem (506) is mounted within the sealing element (512) and is capable of rotary movement about an axis. The valve stem (506) has a recess (508) with an opening (509). In the non-dispensing position shown in FIGS. 16a and 16b there is open communication between the passage (502) and the recess (508) allowing free access of aerosol formulation. As the valve stem (506) is rotated, the opening (509) moves out of line with the passage (502) and thus the opening (509) is blocked by the sealing element (512) thereby forming a closed volume within the recess (508). Further rotation of the valve stem will bring the opening (509) into communication with the discharge passage (504) thereby allowing the contents of the recess (508) to be discharged under the influence of the aerosol propellant.

The valve of FIGS. 16a to 16c has neutral bias since there is no spring biasing means and the pressure of the aerosol formulation does not exert a bias.

In a modification of the valve of FIGS. 16a to 16c (not shown) the valve stem (506) comprises a plurality of recesses (508) circumferentially arranged such that they may be sequentially filled and the contents dispensed by further rotation of the valve stem (506).

Figure 17:
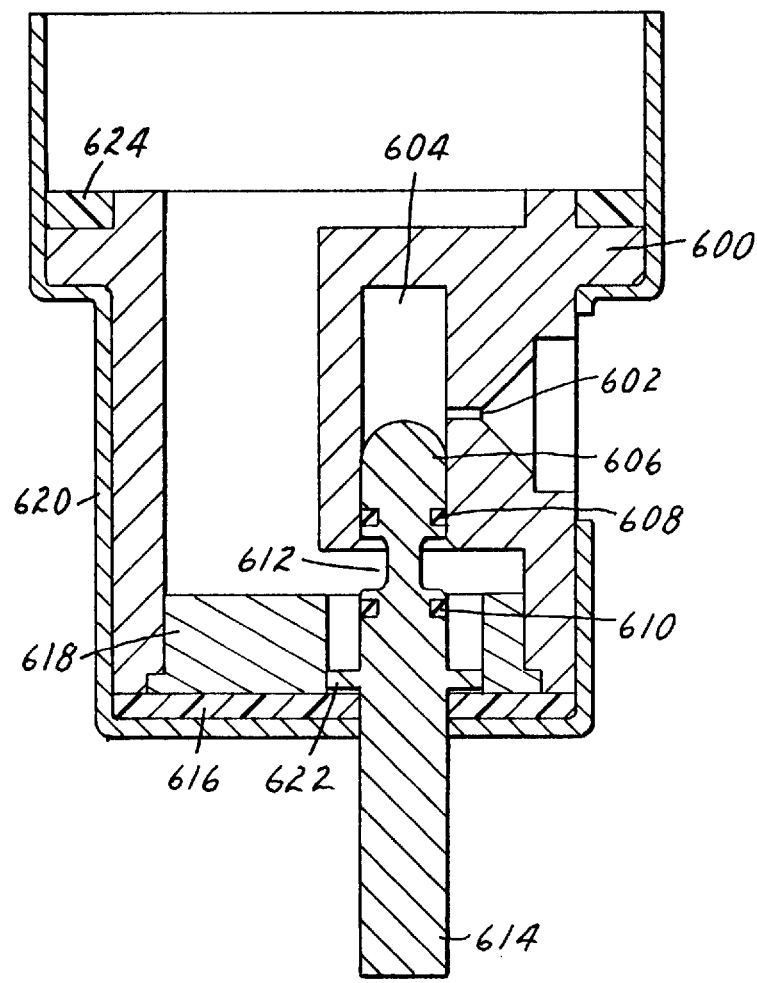
FIG. 17 represents a longitudinal cross-section through a further valve in accordance with the invention.

FIG. 17 discloses a further valve in accordance with the invention in which the valve stem is neither biased towards its dispensing nor its non-dispensing positions, the valve thus being of neutral bias. The valve is also conventionally configured, i.e. being actuated by a pushing-in action. FIG. 17 shows the valve in its priming position.

The valve comprises a nozzle block (600) having an outlet passage in the form of a nozzle (602) for discharge of the pressurised aerosol formulation. The nozzle block (600) defines a chamber (604) in which a valve stem (606) may reciprocally move. The valve stem (606) is extended in the form of a button (614) through a gas-tight seal (616) between a plate (618) attached to the nozzle block (600) and a mounting cup (620) in which the whole valve is contained. A flange (622) on the stem (606) prevents the stem from sliding out of the valve. An annular seal (624) allows the valve to be secured in a gas-tight fashion to an aerosol vial (not shown).

The valve stem (606) additionally comprises annular sealing elements (608, 610) which provide gas-tight seals between the valve stem and the inner wall of the chamber (604). The valve stem (606) is externally configured to have a circumferential groove (612), and the chamber (604) has an internal configuration such that a metered volume is defined therebetween when the button (614) is depressed by the patient far enough to move sealing element (610) into sealing engagement with the inner wall of the chamber (604). Further depression of button (614) by the patient causes sealing element (608) to move past the outlet passage (602), causing a dose of pressurised aerosol formulation to be discharged. The valve is reset by the patient pulling the button (614) back out, to return the valve to its priming position.

In an alternative embodiment, a compression spring (not shown) is positioned between the end of the stem (606) and the closed end of the chamber (604), to return the valve to its priming position when the patient releases the button. Such a valve is biased towards a nondispensing position.

Figure 18:
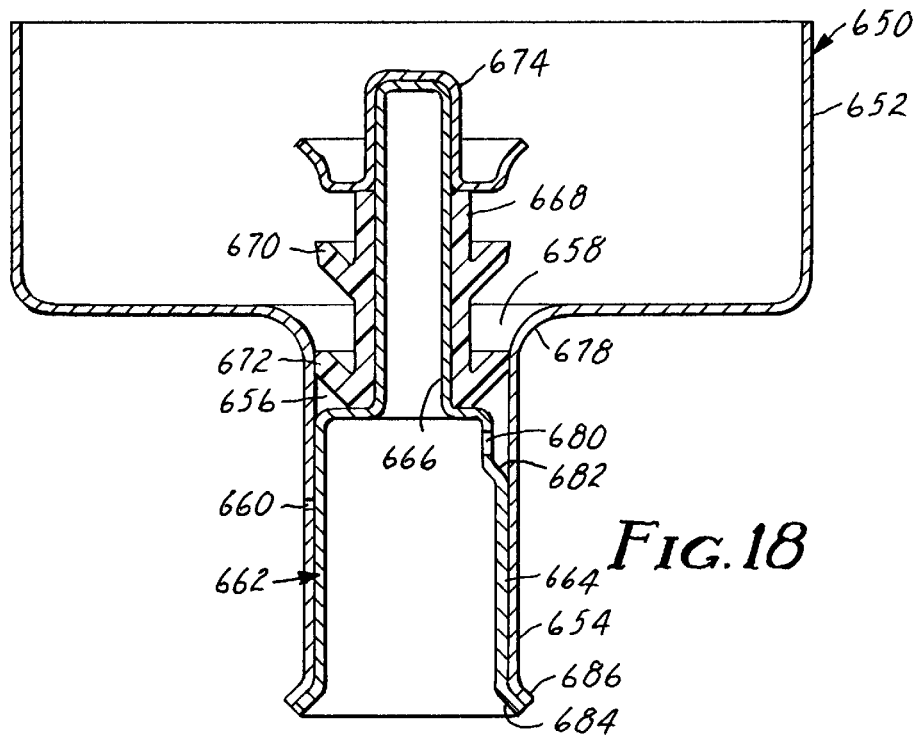
FIG. 18 represents a longitudinal cross-section through a further valve in accordance with the invention illustrating the valve in its non-dispensing position.
Figure 19:
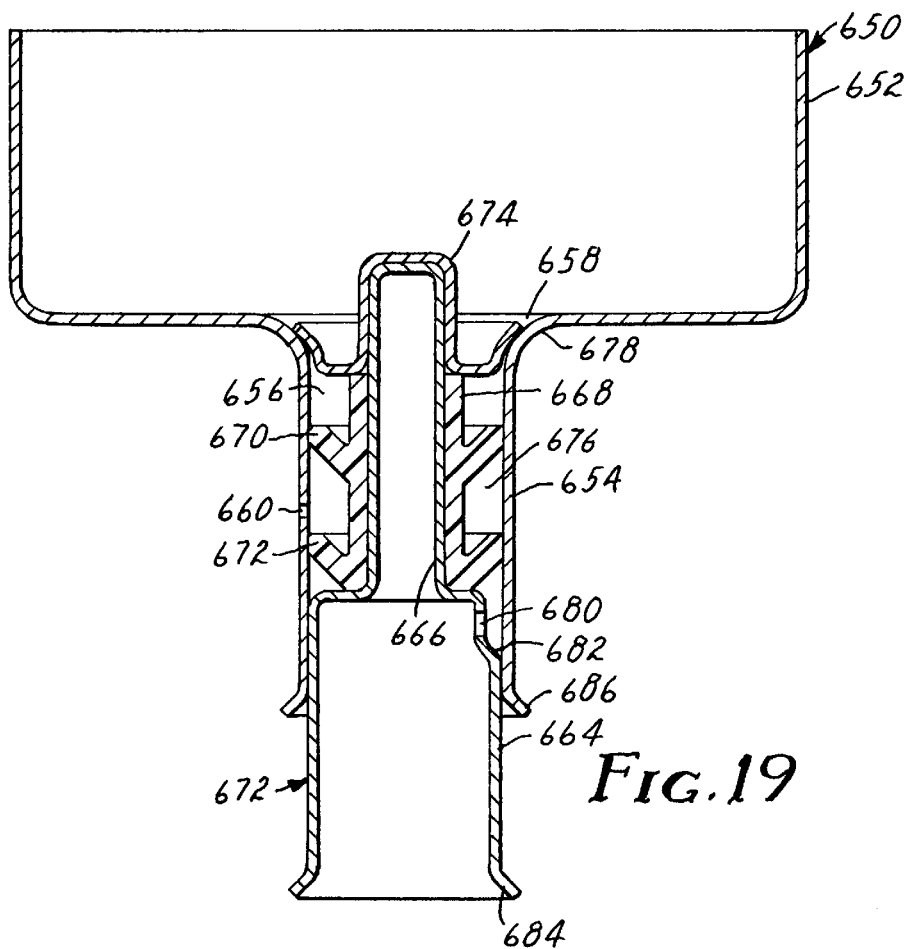
FIG. 19 represents a longitudinal cross-section through the valve of FIG. 18 in its dispensing position.

The valve illustrated in FIGS. 18 and 19 comprises a mounting cup (650) having a circumferential flange (652) for crimping to the neck of a container (not shown) and an elongate portion (654) defining a chamber (656). The chamber (656) has an inlet (658) and an outlet passage (660) in the form of an integral spray orifice which may be formed by a technique such as piercing or drilling or laser cutting. A valve stem (662) is mounted for reciprocal movement with respect to the chamber (656). The valve stem (662) has an outer portion (664) which is dimensioned to be a clearance fit within the chamber (656), and an inner portion (666) having a diameter less than the diameter of the chamber (656). An elastomeric sealing element (668) is fixed around the inner stem portion (666) and comprises two protruding skirt features (670, 672) capable of forming annular gas-tight seals with the internal wall of the chamber (656). A stem cap (674) serves to retain the sealing element (668) and also prevents the valve stem (662) being pushed out of the chamber by the propellent pressure when released. In addition, the stem cap (674) may collect any sedimenting constituents of aerosol formulation to prevent them entering the chamber (656) in excess if the patient forgets to shake the aerosol unit prior to use. The components of the valve other than the sealing element (668) may conveniently be constructed out of deep-drawn metal components which allows simple and economical manufacture.

FIG. 18 shows the valve in its non-dispensing position and FIG. 19 shows the valve in its dispensing position. In its nondispensing position, aerosol formulation has free access to the region of the chamber (656) above the annular seal (672) formed by the skirt feature. As the valve stem moves outwardly towards its dispensing position, the annular seal (670) passes into the chamber, making a gas-tight seal with the walls of the chamber thereby defining a metered volume (688) within the annular gap defined between the skirt features (670, 672) and the wall of the chamber. Further movement of the valve stem (662) causes the annular seal formed by the skirt feature (672) to pass the outlet passage (660) thereby allowing communication between the outlet passage and the metered volume of aerosol formulation (676). Thus, aerosol formulation will be dispensed from the outlet (660).

The valve of the FIGS. 18 and 19 additionally comprises means to allow pressure filling of aerosol formulation into the aerosol container (not shown) after the valve has been crimped to the container. During pressure filling, a filling head is placed over the elongate portion (654) of the mounting cup such that a seal is formed around the radius surface (678) of the valve mounting cup (650) thereby allowing aerosol formulation to be introduced at high pressure into the interior of the valve stem (662). The valve is held in its nondispensing position during pressure filling. The high pressure causes the formulation to pass through a filling port (680) located in a region (682) of the outer stem component (664) which is shaped to provide a space between the outer stem portion (664) and the wall of the chamber (656). The pressure of the formulation causes the annular skirt feature (672) to deflect and temporarily provide a passage allowing access of the aerosol formulation into the aerosol container. The outer end of the valve stem is flared outwardly (684) thereby ensuring the valve stem is not driven into the aerosol container during the pressure filling process. The valve mounting cup (650) is also flared (686) to co-operate with the valve stem during the filling process to prevent jamming of the valve stem.

Figure 20:
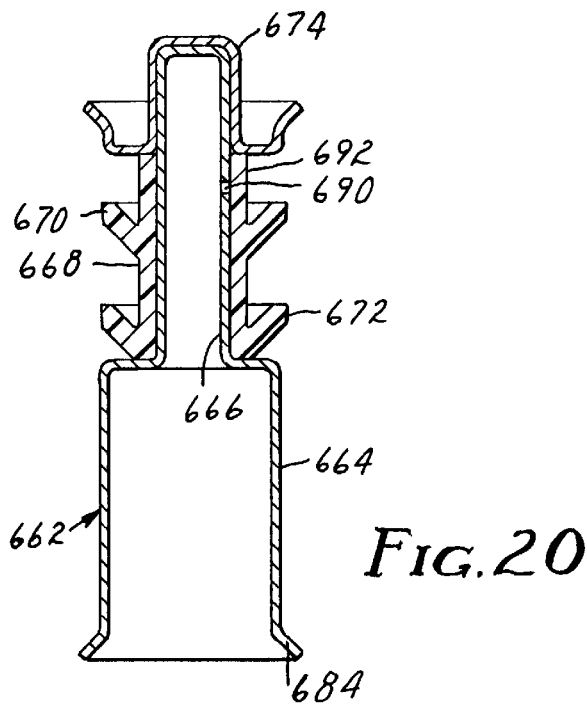
FIG. 20 represents a longitudinal cross-section through an alternative valve stem suitable for use in the valve illustrated in FIGS. 18 and 19.

FIG. 20 illustrates an alternative valve stem suitable for use in the valve disclosed in FIGS. 18 and 19. The valve stem has a different arrangement for pressure filling in the form of a filling port (690) positioned in the wall of the inner portion (666) of the valve stem in a position towards the end (692) of the sealing element (668). When aerosol formulation is introduced under pressure into the valve stem the end (692) of the sealing element (668) is temporarily displaced from the filling port (690) thereby allowing the aerosol formulation to enter the aerosol container (not shown).

Figure 21:
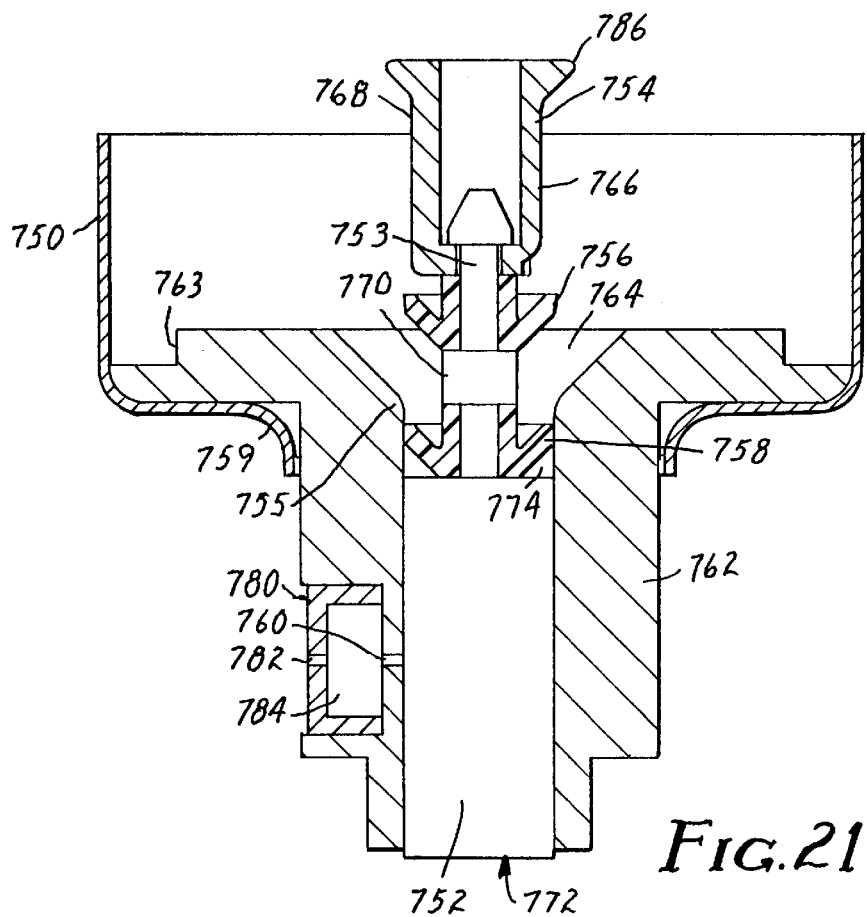
FIG. 21 represents a longitudinal cross-section through a further valve in accordance with the invention.

The valve illustrated in FIG. 21 comprises a mounting cup (750) and a body component (762) which defines a chamber (774). The body component (762) has an annular depression (763) to accommodate a sealing gasket (not shown) to seal the valve to an aerosol container (not shown). A valve stem (772) is positioned for reciprocal movement relative to the chamber (774). The valve stem (772) comprises an outer portion (752) positioned within the chamber and an inner component (753). Two skirted elastomeric sealing components (756, 758) are mounted on the inner portion (753) of the stem on either side of a larger diameter spacer (770). The sealing element (756) is secured in position on the valve stem by retaining component (754). The sealing element (756, 758) are capable of forming annular gas-tight seals with the internal wall of the chamber (774). The valve is shown in its non-dispensing position in FIG. 21 which allows free access of aerosol formulation into the chamber (774) above the sealing element (758).

The valve operates in a similar manner to that disclosed in FIGS. 18 and 19. As the valve stem (772) moves outwardly towards its dispensing position (not shown) the sealing element (756) passes into the chamber (774) making a gas-tight seal with the walls of the chamber thereby defining a metered volume of formulation between the seals (756, 758) and the wall of the chamber. Further movement of the valve stem (772) causes the sealing element (758) to pass an outlet passage (760) thereby allowing communication between the outlet passage (760) and the metered volume of aerosol formulation thus allowing dispensing of the metered volume of aerosol formulation under the influence of the pressure of the aerosol propellant. A flared portion (786) of the retaining component (754) abuts the shoulder (755) of the valve body component (762) thereby preventing the valve stem (772) from being forced out of the chamber under the propellant pressure. The outlet passage (760) may be of a suitably small diameter, e.g. 0.2 to 0.6 mm to ensure a large proportion of the emerging spray is in the form of droplets or particles of a suitable size to be inhaled into the lungs of the patient. The arrangement shown in FIG. 21 additionally comprises a push-in nozzle component (780) comprising a small diameter spray orifice (782) and defining an expansion chamber (784) between the outlet passage (760) and the spray orifice (782). This arrangement allows a larger outlet passage (760) to be used. The expansion chamber may be beneficial for forming a fine easily respirable aerosol spray.

The valve additionally comprises means to allow pressure filling of aerosol formulation through the valve. During pressure filling, a filling head (not shown) is placed over the valve such that a seal is formed around the radius surface (759) of the valve mounting cup (750) thereby allowing aerosol formulation to be introduced at high pressure through the outlet passage (760). This can be done before the nozzle component (780) is fitted into the valve body component. Alternatively, a separate, larger orifice (not shown) diametrically opposite the outlet passage (760) and at the same distance along the valve body component (762) could be used for pressure filling and thereafter sealed with a plug before use of the aerosol by the patient.

Such pressure filling can take place either with the valve in its dispensing or non-dispensing positions. In the dispensing position, aerosol formulation is introduced through the outlet passage (760) causing the sealing element (756) to be deflected inwardly thereby allowing formulation to pass into the aerosol container via one or more grooves (766) in the retaining component (754). The sealing element (758) will remain sealed due to the directional action of the applied filling pressure. The flared parts (786) of the retaining component (754) abuts on the shoulder (755) of the valve body component during the pressure filling, thereby preventing the valve stem from being forced out of the valve.

During pressure filling with the valve in its non-dispensing position, the aerosol formulation is introduced through the outlet passage (760) and passes between the outer portion (752) of the valve stem and the wall of the chamber (774) causing inwards deflection of the annular seal (758) allowing the aerosol formulation to pass into the aerosol container (not shown). The outer component (752) of the valve stem may be provided with a groove (not shown) to facilitate passage of the aerosol formulation from the outlet passage during pressure filling. In this method of pressure filling, the outer portion of the valve stem (752) must be held to restrain the valve stem from being driven into the aerosol container during the pressure filling process.

Figure 22:
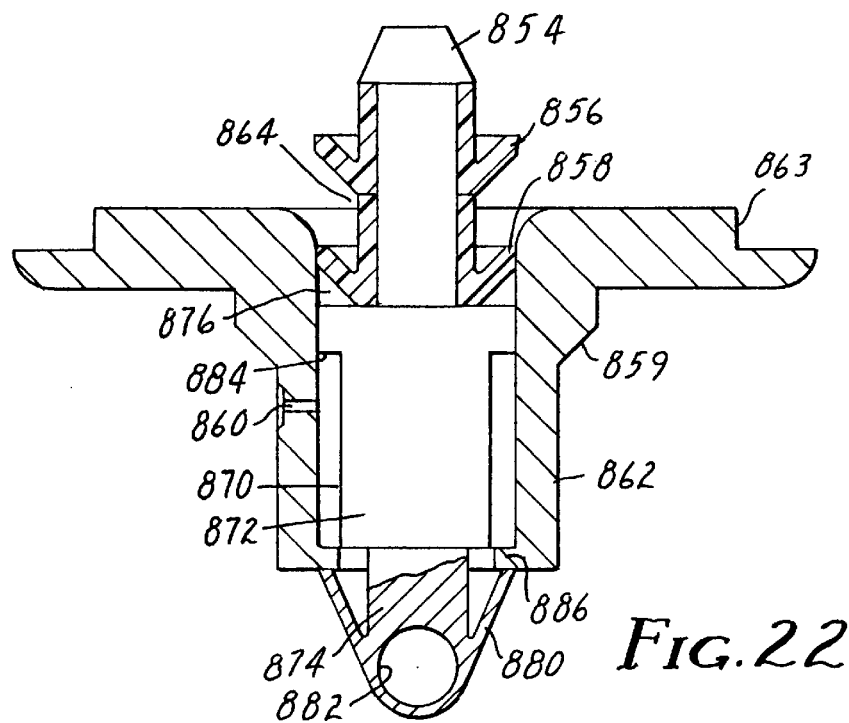
FIG. 22 represents a longitudinal cross-section through a further valve in accordance with the invention with the valve shown in its non-dispensing position.
Figure 23:
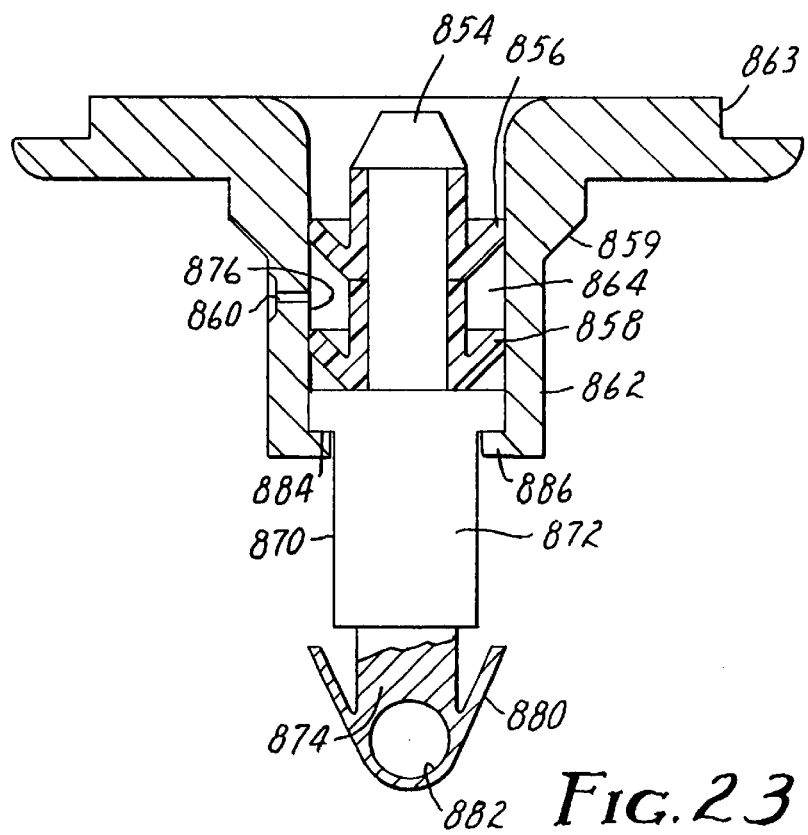
FIG. 23 represents a longitudinal cross-section through the valve of FIG. 22 in its dispensing position.
Figure 24:
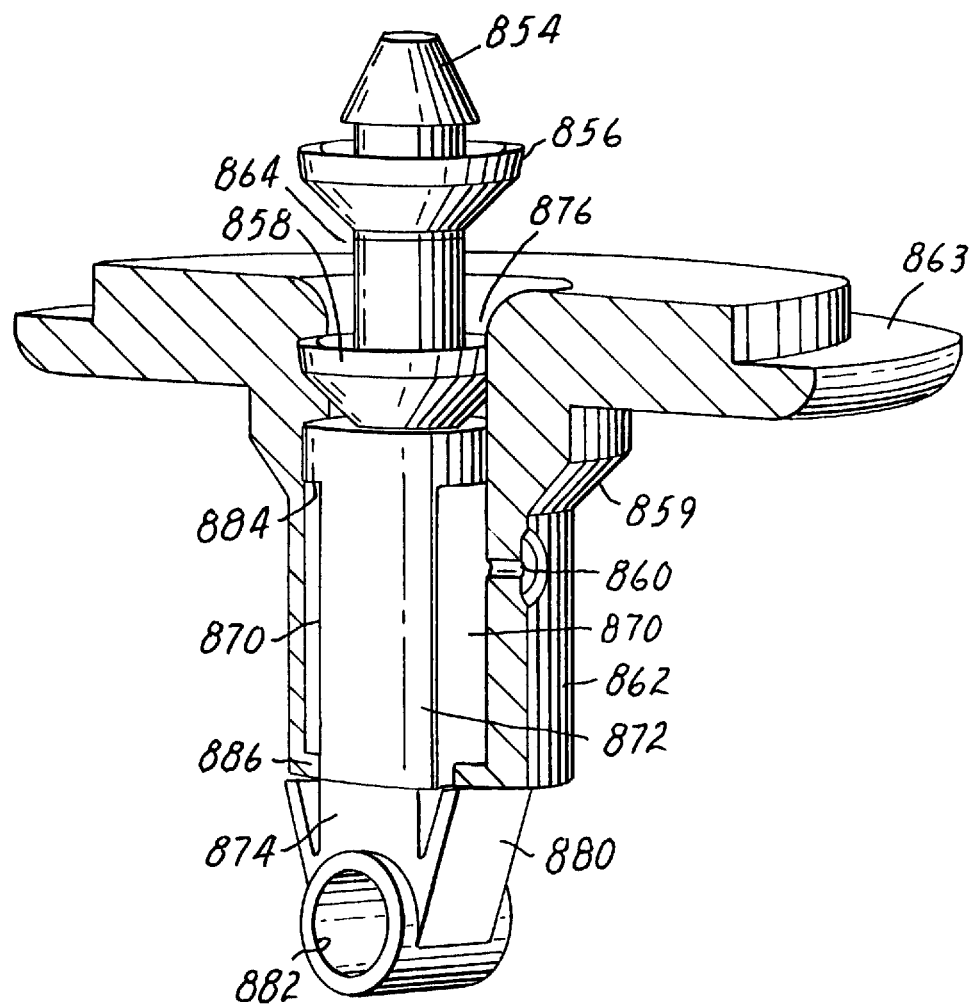
FIG. 24 represents an isometric view of the valve of FIGS. 22 and 23.

The valve illustrated in FIGS. 22 to 24 comprises a mounting cup (not shown), a body component (862) having an annular depression (863) to accommodate a sealing gasket (not shown) to seal the valve to an aerosol container (not shown), a chamber (876) and an outlet passage (860) in the form of an integral spray orifice. A valve stem (872) is positioned for reciprocal movement relative to the chamber and comprises a stem core component (874) and two skirted elastomeric seals (856, 858) fixedly mounted round a narrow portion of the stem core component (874), such that the seals (856, 858) are capable of forming annular gas-tight seals with the internal wall of the chamber (876). The stem core component (874) is shaped to locate the seals in the correct position on the stem after they have been pushed over a retaining feature (854) at the inner end of said stem core component. The stem also comprises moulded features (880) that serve as barbs to prevent the valve stem (872) being pushed into the aerosol container by the filling pressure applied during pressure filling. The valve is shown in FIG. 22 in its non-dispensing position which allows free access of aerosol formulation to the annular gap (864) between the seals (856, 858) and is shown in its dispensing position in FIG. 23.

As the valve stem (872) moves outwardly towards its dispensing position the upper seal (856) passes into the chamber (876) making a gas-tight seal with the inner wall of the valve body component (862), thereby defining a metered volume of aerosol formulation within the annular gap (864). Further movement of the valve stem (872) causes the lower seal (858) to pass the outlet passage (860) thereby allowing communication between the outlet passage (860) and the metered volume of aerosol formulation within the annular gap (864), thus allowing dispensing of the aerosol formulation within said annular gap via the outlet passage (860) under the influence of the pressure of the aerosol propellant.

An external breath-actuated triggering and valve reset mechanism may be connected with the circular feature (882) on the end of the valve stem (872). If the orifice that forms the outlet passage (860) is of suitably small diameter, e.g. 0.2 to 0.6 mm, a large proportion of the particles of the emerging spray may be fine enough to be inhaled into the lungs of the patient.

The valve illustrated in FIGS. 22 to 24 additionally comprises features to allow pressure filling of the aerosol formulation into the aerosol container (not shown) after the valve has been crimped onto the container. During pressure filling, a filling head (not shown) is placed over the valve such that a seal is formed around the angled surface (859) of the valve body component (862) allowing aerosol formulation to be introduced at high pressure through the grooves formed between the planar portions (870) of the stem core component (874) and the internal wall of the valve body component (862). The aerosol formulation then causes the outer seal (858) to deform inwards from the wall of the chamber (876) and thus temporarily unseal, thereby allowing the aerosol formulation to pass into the aerosol container. Ridges (884) at the end of the planar portions (870) serve to prevent the stem from being forced out of the valve by the propellant pressure in the aerosol container by catching on inner rim parts (886) at the end of the valve body component (862).

Figure 25:
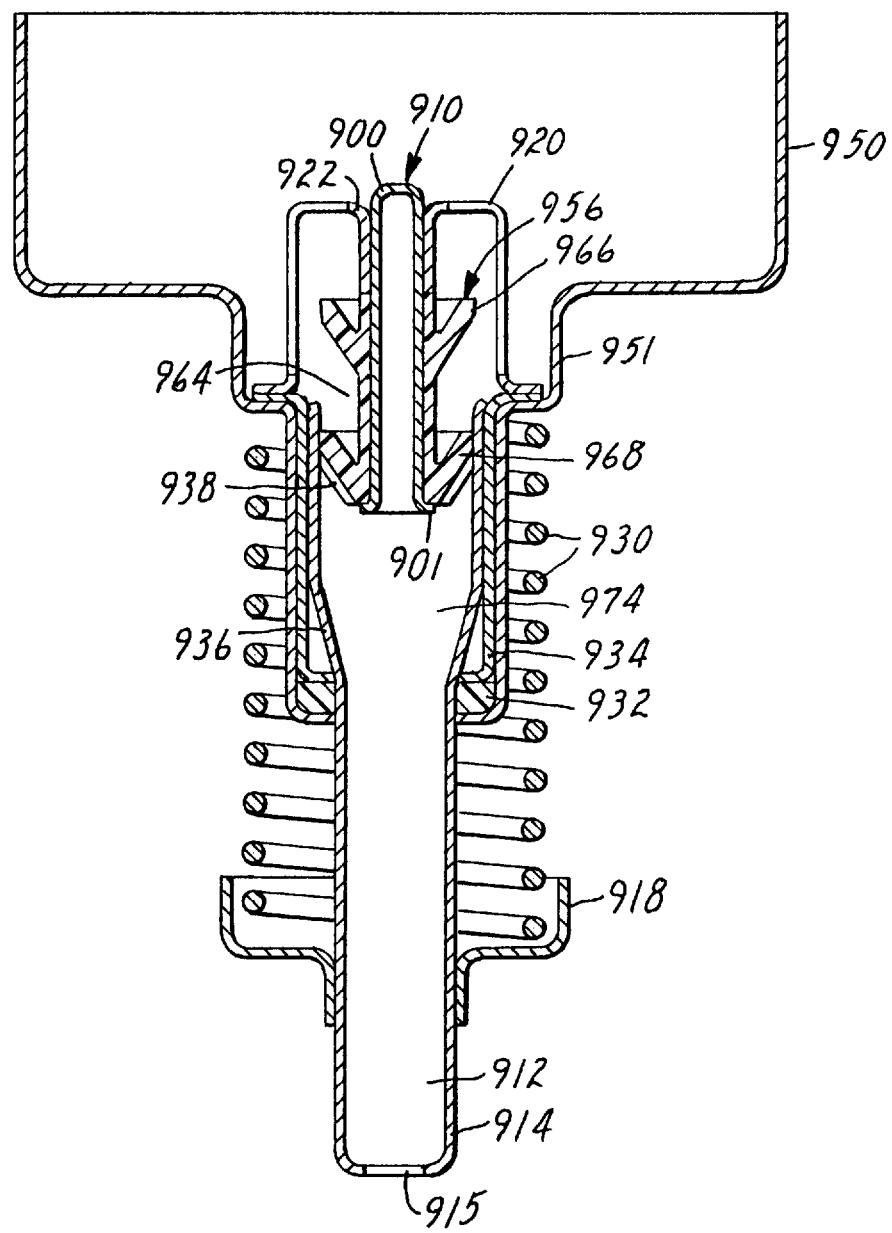
FIG. 25 represents a longitudinal cross-section through a further valve in accordance with the invention.

The valve illustrated in FIG. 25 employs a stationary valve stem and a movable chamber. The valve stem (910) comprises a metal stem component (900) having a flanged end (901) and an elastomeric sealing element (956) fixed on the metal stem component and having two protruding skirt seals (966, 968) capable of forming annular gas-tight seals with the internal wall of the chamber (974). The stem (910) is held in position in the valve by a cage (922) provided with large slots (920) to allow free access of aerosol formulation into the annular space (964) between the protruding skirt seals (966, 968). At the outer end of the chamber is an outlet passage (912) in an outer tube (914) communicating with the chamber (974). An orifice (915) in the end of the outlet passage (912) is provided for aerosol spray release. The cage (922) also serves to locate the sealing element (956) on the metal stem component (900). The cage is held in position in the valve metering cup (950) by a crimp formed at position (951). The crimp also serves to locate a metal hold-down component (934) which holds an annular sealing element (932) in sealing engagement with the metering cup (950), the outer tube (914), and said metal hold-down component (934). A collar (918) fixedly mounted as an interference fit on the outside of the outer tube (914) serves to locate the outer end of a compression spring (930). The other end of said spring bears against the outer surface of said metering cup (950). The valve is designed to be conveniently constructed out of metal components, apart from the elastomeric double skirted sealing element (956), to allow simple and cheap construction.

The valve is shown in FIG. 25 in the closed position in which aerosol formulation has free access to the annular space (964) between the protruding skirt seals (966, 968). In operation, the outer tube (914) and chamber (974) are moved inwardly relative to the valve stem (910) causing upper protruding skirt seals (966) to enter the chamber thereby trapping a metered volume of aerosol formulation in the annular gap (964). Further movement of the chamber causes a sloping wall section (936) to bear against ribs (938) on the seal (968), thereby causing the seal (968) to deflect inwards towards the metal stem component (900). The deflection allows communication between the outlet passage (912) and the annular gap (964) thereby allowing aerosol formulation to pass through the orifice (915) in the end of the outlet passage (912). When the outer tube (914) is released, the spring (930) causes the valve to return to its closed position.

Figure 26:
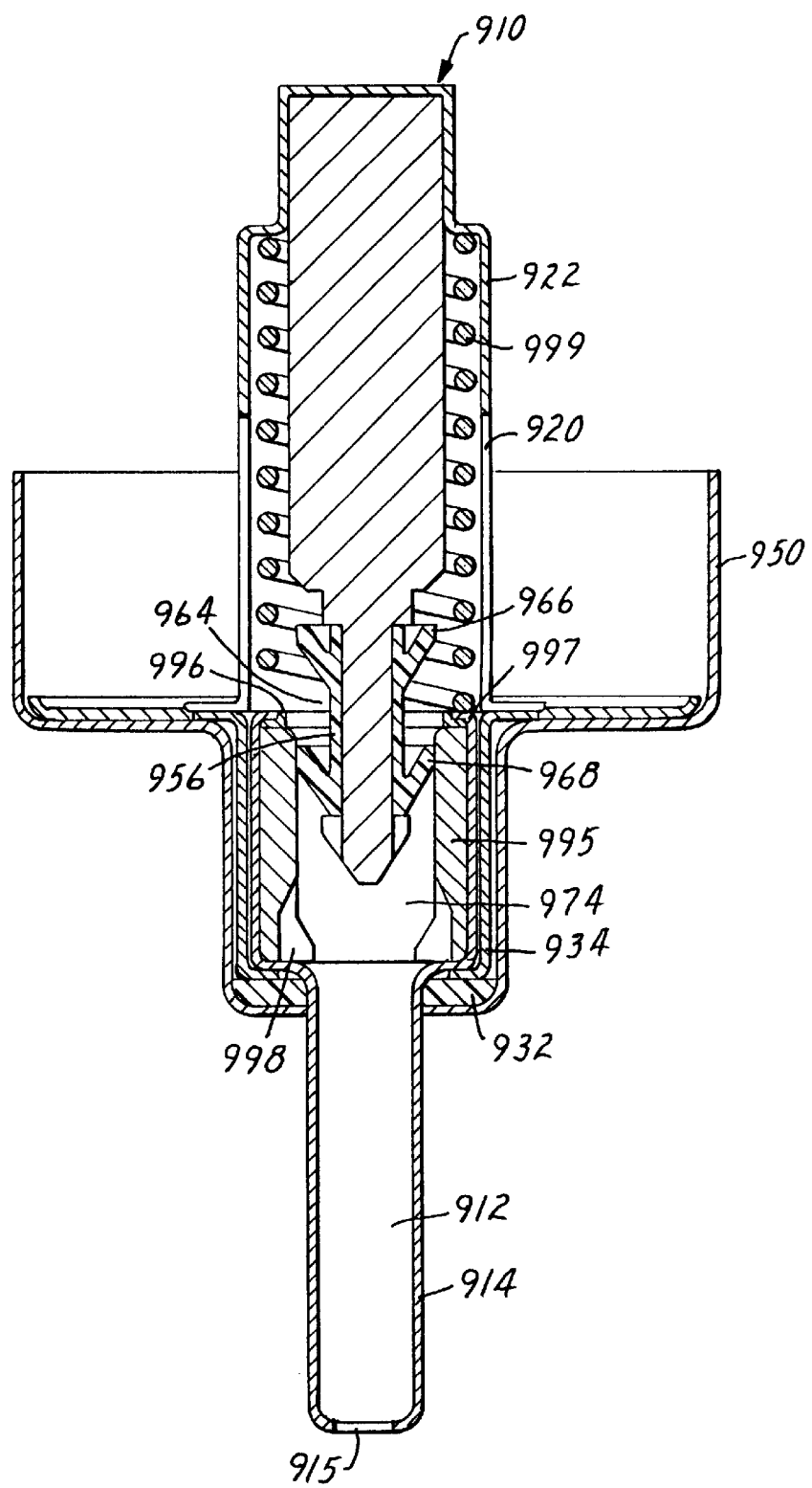
FIG. 26 represents a longitudinal cross-section through a further valve in accordance with the invention.

The valve illustrated in FIG. 26 is similar to that shown in FIG. 25, and like numerals represent like features. In the valve of FIG. 26, however, an extra plastic insert (995) is fixed within the top of the outer tube (914) by means of a turned over flange (997) and the plastic insert defines the chamber (974). An annular sealing component (996) forms a seal with the plastic insert and with the outer tube. The two protruding skirt seals (966, 968) are capable of forming annular gas-tight seals with the internal wall of the chamber (974) defined in the plastic insert (995). At the outer end of the plastic insert is a passage (998) in the form of one or more longitudinally extending recesses. The return spring (999) is internal to the valve, being constrained between the flange (997) on the outer tube (914) and the cage (922).

We claim:

1. A metered dose dispensing valve for dispensing metered volumes of a pressurized aerosol formulation, the valve comprising:

a chamber, an outlet passage and a valve stem extending into the chamber and movable relative to the chamber between non-dispensing and dispensing positions, the valve stem having a configuration including an external surface and the chamber having an internal configuration including an internal surface such that a movable metered volume of pressurized aerosol formulation is capable of being defined therebetween and such that during movement between its non-dispensing and dispensing positions the valve stem sequentially:

(i) allows free flow of aerosol formulation into and out of the chamber, (ii) defines a closed metered volume for pressurized aerosol formulation between the external surface of the valve stem and internal surface of the chamber, and (iii) moves with the closed metered volume within the chamber without decreasing the volume of the closed metered volume until the metered volume communicates with the outlet passage thereby allowing dispensing of the metered volume of pressurized aerosol formulation.

2. A dispensing valve according to claim 1 comprising a housing having a wall defining the chamber, the chamber having an outlet and an inlet having dimensions sufficient to allow free flow of aerosol formulation into and out of the chamber depending upon the orientation of the valve under the effect of gravity without the flow of aerosol formulation being significantly impeded, the valve stem comprising first and second sealing surfaces longitudinally spaced, each sealing surface capable of forming a gas-tight seal with the wall of the chamber, the valve stem and the chamber being configured such that during movement of the valve stem between the non-dispensing and dispensing positions the valve stem sequentially passes:
(i) a priming position in which the inlet is open allowing free access of aerosol formulation to the chamber and the first sealing surface prevents access of aerosol formulation to the outlet,
(ii) a metering position in which the second sealing surface blocks the inlet and the first sealing surface prevents access of aerosol formulation to the outlet, thereby defining a closed metered volume between the first and second sealing surfaces and the wall of the chamber,
(iii) a shuttling stage during which the valve stem moves with the closed metered volume within the chamber without decreasing the volume of the closed metered volume, to
(iv) a dispensing position in which the first sealing surface is positioned to allow access of aerosol formulation to the outlet.

3. A metered dose dispensing valve according to claim 1 wherein said closed metered volume remains at constant volume during movement to the dispensing position.

4. A metered dose dispensing valve according to claim 2 wherein said sealing surfaces comprise sealing elements having one or more lobes, tapered projections or an annular skirt in contact with the wall of the chamber to facilitate sealing without incurring high frictional forces.

5. A metered dose dispensing valve according to claim 4 wherein the sealing elements comprise a central cylindrical portion having an annular skirt inclined with respect to said central cylindrical portion which forms a circumferential sealing surface, said skirt being resiliently flexible such that pressure applied to one side of the skirt urges the circumferential sealing surface radially outwardly to facilitate sealing and pressure applied to the other side of the skirt deflects the circumferential sealing surface radially inwardly.

6. A metered dose dispensing valve according to claim 4 wherein said sealing elements are retained within circumferential grooves on the valve stem and said grooves are configured to provide free space to accommodate movement of said sealing elements when they are deformed.

7. A metered dose dispensing valve according to claim 1 wherein said valve stem comprises at least one recess and the wall of the chamber comprises an elastomeric sealing surface making a gas-tight seal with the valve stem, said sealing surface extending longitudinally a greater distance than said recess on the valve stem whereby said closed metered volume is defined by said recess and said sealing surface.

8. A metered dose dispensing valve according to claim 7 wherein said wall of the chamber is formed of elastomeric sealing material retained by upper and lower support members and said elastomeric sealing material comprises fins bearing against at least one of the support members to allow flexing of the sealing material.

9. A metered dose dispensing valve according to claim 2 wherein said valve stem comprises at least one recess positioned between said first and second sealing surfaces such that said closed metered volume is defined between said recess, said first and second sealing surfaces and the wall of the chamber.

10. A metered dose dispensing valve according to claim 2 wherein a spray orifice is integrally formed with said outlet passage or is in communication with said outlet passage to allow aerosol formulation to be dispensed as a spray.

11. A metered dose dispensing valve according to claim 1 wherein said valve stem moves inwardly from its non-dispensing to dispensing position.

12. A metered dose dispensing valve according to claim 1 wherein said valve stem moves outwardly from its non-dispensing to dispensing position.

13. A metered dose dispensing valve according to claim 2 wherein said valve stem is biased to its dispensing position or nondispensing position by a spring or pressure generated by said aerosol formulation.

14. A metered dose dispensing valve according to claim 1 wherein said valve stem is capable of rotary movement between its non-dispensing and dispensing positions.

15. A metered dose dispensing valve according to claim 1 fitted on an aerosol container wherein said aerosol container contains pressurized aerosol formulation.

16. A metered dose dispensing valve and container according to claim 15 in the form of an inhaler wherein the aerosol formulation comprises medicament.

17. A metered dose dispensing valve and container according to claim 16 wherein the inhaler comprises patient inhalation means responsive to patient inhalation, actuation means to move the valve stem to its dispensing position and triggering means responsive to the patient inhalation means such that the actuation means is triggered by patient inhalation.

18. A valve according to claim 2 comprising means to allow aerosol formulation to be pressure-filled through said outlet passage or a pressure filling port located in the valve stem.

* * * * *